(12) United States Patent
Javadi

(10) Patent No.: US 10,338,897 B2
(45) Date of Patent: Jul. 2, 2019

(54) VISUAL PROTOCOL DESIGNER

(71) Applicant: Stratedigm, Inc., San Jose, CA (US)

(72) Inventor: Shervin Javadi, Monte Sereno, CA (US)

(73) Assignee: Stratedigm, Inc., San Jose, CA (US)

( * ) Notice: Subject to any disclaimer, the term of this patent is extended or adjusted under 35 U.S.C. 154(b) by 115 days.

(21) Appl. No.: 15/449,833

(22) Filed: Mar. 3, 2017

(65) Prior Publication Data

US 2018/0253194 A1 Sep. 6, 2018

(51) Int. Cl.
*G06F 8/34* (2018.01)
*G06F 3/0484* (2013.01)
*G06F 3/0486* (2013.01)
*G01N 15/14* (2006.01)

(52) U.S. Cl.
CPC .............. *G06F 8/34* (2013.01); *G06F 3/0484* (2013.01); *G06F 3/0486* (2013.01); *G06F 3/04847* (2013.01); *G01N 15/14* (2013.01); *G01N 15/1425* (2013.01)

(58) Field of Classification Search
CPC ...... G06F 8/34; G06F 3/0484; G06F 3/04847; G06F 3/0486
See application file for complete search history.

(56) References Cited

U.S. PATENT DOCUMENTS

| | | | | |
|---|---|---|---|---|
| 5,623,592 A * | 4/1997 | Carlson | .................... | G06F 8/34 700/83 |
| 5,841,959 A * | 11/1998 | Guiremand | ............ | B25J 9/1671 345/440 |
| 6,326,147 B1 * | 12/2001 | Oldham | ............. | G01N 35/0092 435/6.12 |
| 6,760,842 B1 * | 7/2004 | Miller | ...................... | G06F 8/34 715/763 |
| 7,886,264 B1 * | 2/2011 | Peyton | ...................... | G06F 8/34 709/201 |
| 2008/0006535 A1 * | 1/2008 | Paik | .................. | B01L 3/502792 204/600 |
| 2008/0281471 A1 * | 11/2008 | Smith | ................. | B01F 13/0071 700/266 |
| 2014/0304637 A1 * | 10/2014 | Ijiri | ...................... | G06F 3/04842 715/771 |

\* cited by examiner

*Primary Examiner* — Justin R. Blaufeld
(74) *Attorney, Agent, or Firm* — Kilpatrick Townsend & Stockton LLP

(57) ABSTRACT

Disclosed is a graphical user interface to quickly build a graphical representation defining the set of instructions in a protocol without the user needing the programming knowledge to encapsulate those instructions in executable code. The graphical representation may include an arrangement of one or more graphical elements, with each graphical element corresponding to instructions or program logic. The user may also specify the set of parameters associated with each of the graphical elements. The arrangement of the one or more graphical elements, along with the set of parameters for each of the graphical elements, may be used to translate the graphical representation of the protocol into executable code for the protocol. The executable code for the protocol may then be executed by various flow cytometry machines in order to perform the protocol.

19 Claims, 24 Drawing Sheets

Graphical Representation of a Protocol 410

Arrangement:

| Icon 1-1 | Icon 1-2 | ... | Icon 1-N |
| Icon 2-1 | Icon 2-2 | ... | Icon 2-N |
| ... | ... | ... | ... |
| Icon N-1 | Icon N-2 | ... | Icon N-N |

412-1, 412-2, 412-N

↕ Translation

Executable Code for Protocol 420

```
...
set incubator.temperature.celsius = 37 if sheathTankIsEmpty == 1
    set limitDuration = 1
    set maxSeconds = 420
    perform refillSheathTank(limitDuration, maxSeconds)

set wellsAffected = [1, 1, 0, 0, 0, 0, 0, 0, 0, 0, 0, 0;
                     1, 1, 0, 0, 0, 0, 0, 0, 0, 0, 0, 0;
                     0, 0, 0, 0, 0, 0, 0, 0, 0, 0, 0, 0;
                     0, 0, 0, 0, 0, 0, 0, 0, 0, 0, 0, 0;
                     0, 0, 0, 0, 0, 0, 0, 0, 0, 0, 0, 0;
                     0, 0, 0, 0, 0, 0, 0, 0, 0, 0, 0, 0;]

perform addReagent(wellsAffected);

perform mixSample(wellsAffected);

perform addToIncubator();
...
```

FIG. 4

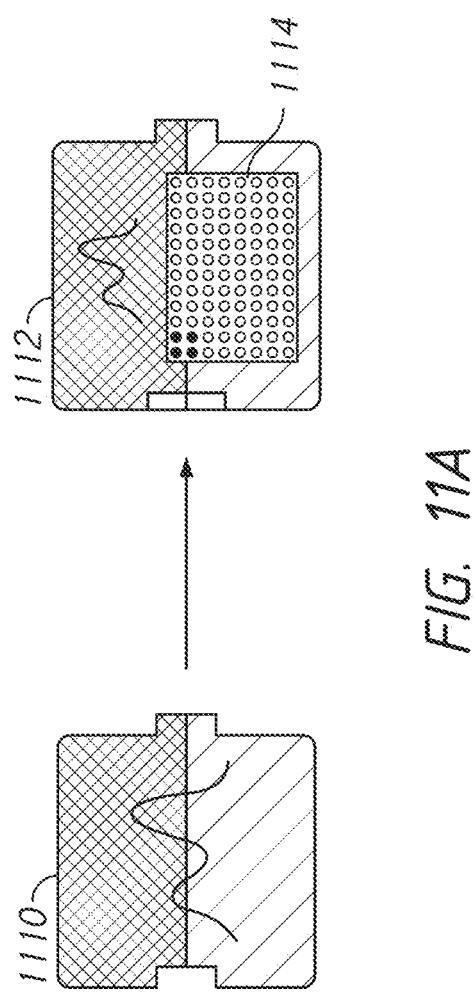

VISUAL PROTOCOL DESIGNER

FIELD

Methods and systems disclosed herein relate generally to flow cytometry machines capable of running executable code to perform a set of instructions or procedures defined in a protocol. More specifically, a user interface can be provided to a user that allows the user to quickly build a graphical representation defining the set of instructions in a protocol without the user needing the programming knowledge to encapsulate those instructions in executable code. The graphical representation can then be automatically translated into executable code, which can then be used by various flow cytometry machines to perform the protocol.

BACKGROUND

In biotechnology, flow cytometry involves the use of lasers and optics to perform cell counting, cell sorting, biomarker detection, and protein engineering. Cells are suspended in a stream of fluid and passed by an electronic detection apparatus, which can analyze the physical and chemical characteristics of the cells and/or other microscopic particles in the fluid. In some cases, fluorescent markers or labels having desired properties may be attached to target features on the cells in order to be used as a quantitative tool.

Modern flow cytometers are able to analyze several thousand particles every second in real-time in order to provide an automated quantification of parameters associated with those particles. Some flow cytometers may also be able to actively sort, separate, and isolate particles having specific properties in order to obtain particle populations of interest.

Flow cytometry is frequently used in the diagnosis of health disorders, as well as in basic research, clinical practice, and clinical trials. For instance, flow cytometry can be used to detect the presence of a specific particle (e.g., a pathogen) in a cell sample. However, in order for a flow cytometer to produce consistent and repeatable results (e.g., reliably identify that specific particle), the components of the flow cytometer may need to follow a set of rules or procedures specifically tailored to sorting, separating, and isolating that particular particle.

A set of these procedures may need to be devised, tested, and implemented into a usable form that can be interpreted by the flow cytometer in order to instruct the components of the flow cytometer to follow the set of procedures. Implementing the set of procedures may involve encapsulating the set of procedures into a programming language that can be interpreted by the flow cytometer. However, expressing the set of procedures in the programming language may be a difficult and time-consuming task, which involves having to learn the programming language to program the set of procedures. This implementation time would be in addition to the time also needed for devising and testing the set of procedures. As a result, the users of flow cytometry machines frequently do not have the time or capacity needed to create these sets of procedures and those tasks are often left to specialists.

Thus, there exists a need for a quicker and easier way to devise, test, and implement sets of procedures usable by a flow cytometry machine. This would improve the development time for these sets of procedures and could potentially improve the health outcomes of hundreds of thousands of people across the world, such as in the case of generating a set of procedures for reliably identifying a new pathogen for the purposes of diagnosis.

BRIEF SUMMARY

Disclosed is a graphical user interface that allows a user to quickly build a graphical representation defining the set of instructions in a protocol without the user needing the programming knowledge to encapsulate those instructions in executable code. The graphical representation may include an arrangement of one or more graphical elements, with each graphical element corresponding to instructions or program logic. To build the graphical representation, the user may select these graphical elements from a tool palette or bank of graphical elements. The user may also set various parameters associated with each of the selected graphical elements, and the set of parameters for each graphical element may affect how the instructions associated with that graphical element are executed.

The user may manipulate the arrangement of selected graphical elements by ordering them in a desired sequence. The arrangement of the selected graphical elements, along with the set of parameters for each of the graphical elements, may be used to translate the graphical representation of the protocol into executable code for the protocol. The executable code for the protocol may then be executed by various flow cytometry machines in order to perform the protocol.

Accordingly, the present inventive disclosure discusses various methods for programming protocols which are usable by flow cytometry machines. These methods may include generating a graphical user interface (GUI) to be displayed to a user, with the GUI including a workspace and a bank. The bank can include a plurality of selectable graphical elements, with each selectable graphical element in the bank corresponding to program logic. Each of the selectable graphical elements in the bank can be dragged over to the workspace based on user inputs.

For example, these methods may include receiving a first user input for dragging a first selectable graphical element from the bank to the workspace of the GUI and receiving a second user input for dragging a second selectable graphical element from the bank to the workspace of the GUI. Once the first and second selectable graphical elements have been dragged to the workspace of the GUI, the workspace of the GUI can be updated to display a graphical representation for a protocol that includes an arrangement of the first and second selectable graphical elements. This arrangement of the graphical representation conveys a sequence for performing the program logic corresponding to the first selectable graphical element and the second selectable graphical element (and any other graphical elements added to the arrangement, there can be more than two). This sequence of the arrangement is used to translate the graphical representation for the protocol into one or more executable instructions usable by a flow cytometry machine to perform the protocol, with the one or more executable instructions following the sequence for performing the program logic corresponding to the first selectable graphical element and the second selectable graphical element that conveyed by the graphical representation. For example, if the first selectable graphical element precedes the second selectable graphical element in the arrangement of the graphical representation of the protocol, then the program logic for the first selectable graphical element would be executed first. In some embodiments, the one or more executable instructions are configured to be translated back into the graphical representation for the protocol to be displayed in the GUI for additional editing of the graphical representation for the protocol.

In some embodiments, the program logic corresponding to at least one of the selectable graphical elements in the plurality of selectable graphical elements is a conditional operation. The conditional operation causes any subsequent program logic in the sequence (conveyed by the arrangement of the graphical representation) to be executed only if a condition is met. For example, if the program logic corresponding to the first selectable graphical element is an operation with a conditional statement, and the first selectable graphical element precedes the second graphical element in the sequence, the program logic corresponding to the second selectable graphical element would be performed only if the conditional statement is met.

In some embodiments, the program logic corresponding to at least one of the selectable graphical elements in the plurality of selectable graphical elements sets a reference point within the sequence conveyed by the arrangement of the graphical representation. For example, if the first selectable graphical element is used to set a reference point, the program logic corresponding to other selectable graphical elements can refer to that reference point during the execution of the protocol (e.g., begin a timer at the reference point, and so forth).

In various embodiments, the program logic corresponding to at least one of the selectable graphical elements in the plurality of selectable graphical elements may control various aspects of components of the flow cytometry machine. For example, program logic corresponding to at least one of the selectable graphical elements may control a temperature associated with a component in the flow cytometry machine, or it may control an incubation period for a plate handled by the flow cytometry machine, or it may control recordation of contents of a plate handled by the flow cytometry machine, or it may control mixing of contents of a plate handled by the flow cytometry machine, or it may control the addition of a reagent to a plate handled by the flow cytometry machine.

In some embodiments, the GUI may have a preview window that displays to the user how the protocol would be executed based on the graphical representation for the protocol. The preview window may be configured to separately display results from the program logic corresponding to the first selectable graphical element and the results from the program logic corresponding to the second selectable graphical element (and so forth).

In some embodiments, each selectable graphical element in the workspace is further configured to be selectable to modify a set of parameters associated with the program logic corresponding with that selectable graphical element. The user can change the set of parameters associated with each selected graphical element, as well as move those selected graphical elements around in the workspace to change their sequence in the arrangement. For example, the first selectable graphical element could be moved within the workspace to change the arrangement of the first and second selectable graphical elements.

In some embodiments, the one or more executable instructions translated from the graphical representation is configured to be executed by different types of flow cytometry machines in order to perform the protocol and produce similar results. The workspace of the GUI may have an additional graphical representation for an additional protocol, and translating the graphical representation for the protocol into one or more executable instructions may also include translating the additional graphical representation for the additional protocol. The one or more executable instructions resulting from the additional graphical representation may be used by the flow cytometry machine to perform the additional protocol sequentially with the first protocol.

These various embodiments are described in detail in conjunction with the following drawings in the paragraphs below.

BRIEF DESCRIPTION OF THE DRAWINGS

FIG. 4 illustrates how a graphical representation of a protocol may be translated into executable code, in accordance with an example embodiment.

FIG. 11A illustrates an example embodiment of a block that a user may use in a graphical representation of a protocol.

FIG. 11B illustrates an example embodiment of a user interface menu for setting parameters associated with a block.

FIG. 12B illustrates an example embodiment of a user interface menu for setting parameters associated with a block.

FIG. 13B illustrates an example embodiment of a user interface menu for setting parameters associated with a block.

FIG. 14B illustrates an example embodiment of a user interface menu for setting parameters associated with a block.

FIG. 16B illustrates an example embodiment of a user interface menu for setting parameters associated with a block.

DETAILED DESCRIPTION

Figure 1:
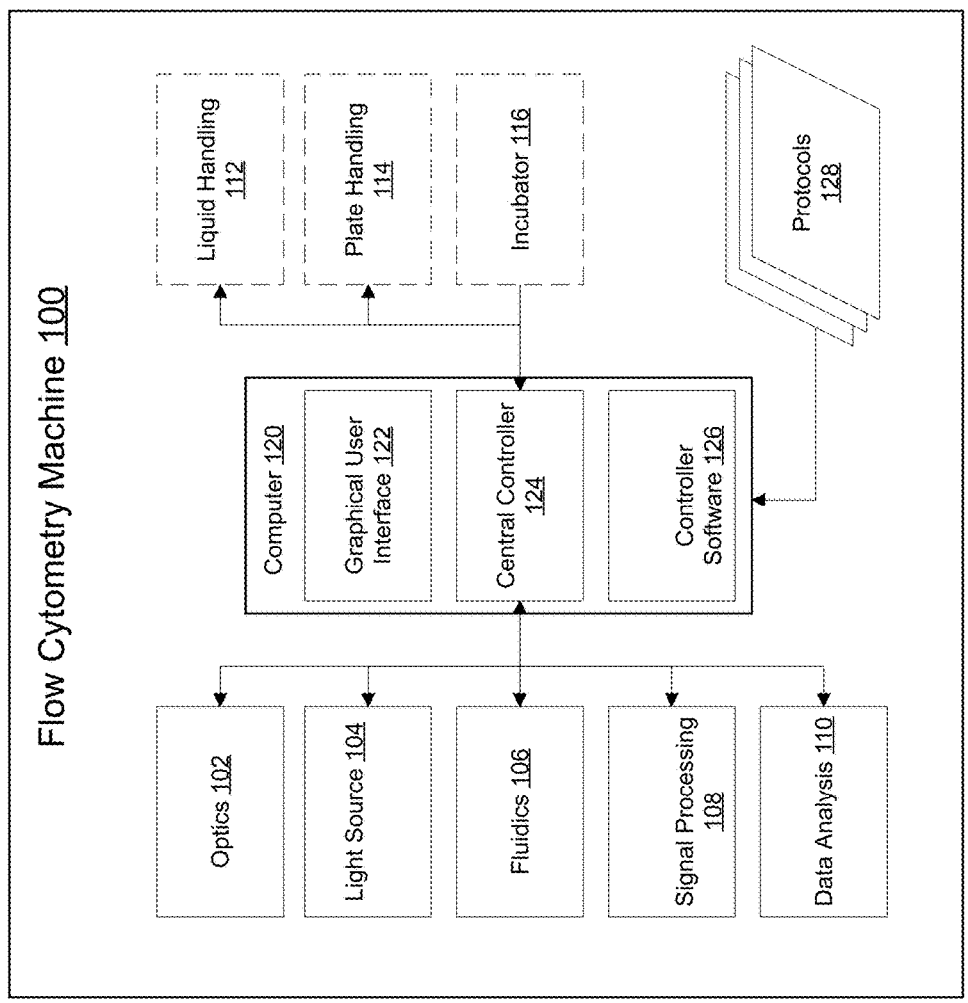
FIG. 1 is a system diagram of a flow cytometry machine that can be managed through the use of a protocol, in accordance with example embodiment.

In the following description, for the purposes of explanation, specific details are set forth in order to provide a thorough understanding of embodiments of the invention. However, it will be apparent that various embodiments may be practiced without these specific details. The figures and description are not intended to be restrictive.

Introduction

Modern flow cytometers are able to analyze several thousand particles every second in real-time in order to provide an automated quantification of parameters associated with those particles. Some flow cytometers may also be able to actively sort, separate, and isolate particles having specific properties in order to obtain particle populations of interest. In order to perform these tasks, the flow cytometers are typically outfitted with common components that include a flow cell, a measuring system, a light detector, an analog to digital system that converts dye-specific fluorescence signals into digital signals processable by a computer, an amplification system, and a computer for analysis of the signals.

The flow cytometer may be configured for detecting, sorting, separating, and isolating particular particles based on instructions provided in a set of rules or procedures that are specifically tailored to that particular particle. This set of rules or procedures may be referred to as a "protocol". For instance, there may be a specific protocol used by flow cytometer to detect a specific kind of bacteria that could be present in a sample containing the cells of a patient. These protocols can be developed by a knowledgeable user of the flow cytometry device (such as a specialist or technician) and then widely disseminated to other flow cytometry users. For instance, the protocols can be uploaded to a server or a cloud computing network where they can be downloaded by other flow cytometry users. The other flow cytometry users can run the protocols to easily detect or quantify the desired particles without "looking under the hood" and knowing the particulars of the protocol.

However, in some embodiments, the development of protocols may be a challenging and time-consuming process that involves devising, testing, and implementing the protocol in a form that is usable by the flow cytometer. For instance, in some embodiments, the flow cytometer may be configured to follow instructions laid out in programming code. In some of such embodiments, the code may be in a programming language that is mainly applicable towards instructing flow cytometry devices. Thus, in order for a user to develop a protocol, the user may have to be familiar with programming concepts and the syntax of the programming language used. The user may also have to understand the best, acceptable practices for designing, devising, and testing a robust protocol that can yield repeatable results. Thus, there may be a substantial burden on the user to have the pre-requisite knowledge needed for developing protocols, on top of the time needed to write and test the protocol.

Accordingly, the present disclosure discloses various embodiments of a visual protocol designer, which is a tool usable for developing protocols for use in flow cytometry applications. More specifically, some embodiments of the visual protocol designer include various graphical user interfaces, such as a drag-and-drop based interface, that allow users to build and design unique and complex protocols for flow cytometry applications without programming knowledge. Users of the visual protocol designer may build multi-line, sequential protocols with conditional operations that can be used to instruct the flow cytometry device to prepare and analyze samples based on various criteria and parameters specified by the user. Since the visual protocol designer allows for the development of protocols without knowledge of programming, it provides for a quicker and easier way to devise, test, and implement the protocols.

Definitions

In order to facilitate an understanding of the systems and methods discussed herein, a number of terms are defined below. The terms defined below, as well as other terms used herein, should be construed broadly to include, without limitation, the provided definitions, the ordinary and customary meanings of the terms, and/or any other implied meanings for the respective terms. Thus, the definitions below do not limit the meaning of these terms, but only provide example definitions.

Protocol: A broad term for any set of instructions, rules, or procedures. The various components of a flow cytometry machine may be controllable to perform a protocol. A protocol may be designed to be followed by a flow cytometry machine in order to produce repeatable results. A protocol may be configured to enable a flow cytometry machine to detect, sort, separate, and/or isolate a particular particle. The set of instructions in a protocol may be encapsulated in the form of executable code, which can be executed by the controller of a flow cytometry machine to automatically carry out the instructions of the protocol. The protocol may also be partially encapsulated in the form of a graphical representation, in which the set of instructions is conveyed through a set of graphical elements that correspond to the instructions and are arranged in a particular sequence.

Translation: The act of converting the graphical representation of a protocol into the form of executable code, or vice versa. The translation may be performed by the system, which may include any component of a flow cytometry machine and/or one or more separate computing devices.

Visual Protocol Designer: A tool that includes one or more user interfaces that allow a user to create a graphical representation of a protocol, which may include one or more graphical elements that are placed in an arrangement. The visual protocol designer may allow a user to select the graphical elements to add to the graphical representation, as well as manipulate those selected graphical elements into a desired arrangement.

Graphical Element: A broad term for any image or symbol that can be selected and manipulated by a user in the visual protocol designer. A graphical element may be associated with program logic that can be used to carry out one or more instructions of a protocol. The terms "graphical element", "block", or "icon" may be used interchangeably and/or synonymously in the present disclosure.

Parameter: A broad term for a user-configurable modifier associated with a graphical element that may modify the program logic associated with that graphical element. For example, a graphical element for "wait" may be associated with a time parameter that defines a wait time. If the program logic for that graphical element is to instruct a component to take a pause, the time attached to that instruction my depend on the time parameter set by the user. Each graphical element may be associated with any number of parameters, which make up a set of parameters associated with that graphical element. The terms "parameter", "property", or "option" may be used interchangeably and/or synonymously in the present disclosure.

Tool Palette: A tool palette is a graphical interface element in the visual protocol designer that displays one or more graphical elements that may be selected by the user and added to the graphical representation of a protocol. The terms "tool palette", "toolbox", and "bank" may be used interchangeably and/or synonymously in the present disclosure.

Workbench: A workbench is a graphical interface element in the visual protocol designer that displays one or more selected graphical elements that may be ordered into an arrangement for the graphical representation of a protocol. A user may be able to select graphical elements by moving the graphical element from the tool palette to the workbench. The terms "workbench" and "workspace" may be used interchangeably and/or synonymously in the present disclosure.

Figures

FIG. 1 illustrates various components of a flow cytometry machine that can be managed through the use of a protocol, in accordance with example embodiments of this application.

More specifically, a flow cytometry machine 100 is shown having an optics component 102, a light source component 104, a fluidics component 106, a signal processing module 108, a data analysis module 110. The flow cytometry machine 100 may also have optional components, such as a liquid handling component 112, a plate handling component 114, and an incubator 116. These components may be communicatively coupled to a central controller 124 of a computer 120 of the flow cytometry machine 100. The central controller 124 may control the various components of the flow cytometry machine 100. There may be controller software 126 that runs on computer 120 and it may be executed by the central controller 124. The controller software 126 may receive input from one or more protocols 128, which provide a set of procedures or a workflow for the flow cytometry machine 100 to perform. Accordingly, the central controller 124 and the controller software 126 may be used in combined to execute the instructions in the one or more protocols 128 in order to control the various components of the flow cytometry machine 100. In some embodiments, there may be a graphical user interface 122 displayed on the computer 120, which allows a user (not shown) to interact with the flow cytometry machine 100. For example, the user may be able to use the graphical user interface 122 to select and configure the one or more protocols 128 or to view the analysis results produced by the flow cytometry machine 100.

In some embodiments, the fluidics component 106 may be referred to as a flow cell. If the flow cytometry machine 100 is tasked with analyzing a sample of cells suspended in fluid, the flow cell may carry and align the cells in the sample so that they pass single file through a light beam (such as the light source component 104) for sensing. In other words, the cells may be placed into a single-file line in order to facilitate counting and analysis of the cells.

In some embodiments, the light source component 104 may be any component capable of producing light signals. For example, in some embodiments, the light source component 104 may be a laser, while in other embodiments, the light source component 104 may be a lamp. The optics component 102 may be configured to focus the light signals for detection, which are amplified and processed by the signal processing module 108. The data analysis module 110 then performs analysis on the processed signals in order to produce quantified metrics that can be understood by a user. In some embodiments, the functions of the signal processing module 108 and/or the data analysis module 110 may be performed by one or more components of the computer 120.

In some embodiments, the flow cytometry machine 100 may optionally include a liquid handling component 112, a plate handling component 114, and an incubator 116, which serve to expand the functionality and operations that can be performed by the flow cytometry machine 100. Examples of such components include the Stratedigm A600 High Throughput Auto Sampler (HTAS), the Stratedigm A700 High Throughput Hotel (HTH), and the Stratedigm A800 Cell Incubator (CI). These components can be used with a Stratedigm S1000Exi/SE520EXi flow cytometer for added functionality and implement more of the protocol instructions described herein. For example, these components may allow the flow cytometry machine 100 to automatically perform analysis using samples that are stored in the wells of a plate, which can be taken out of the incubator at a specified time.

Figure 2:
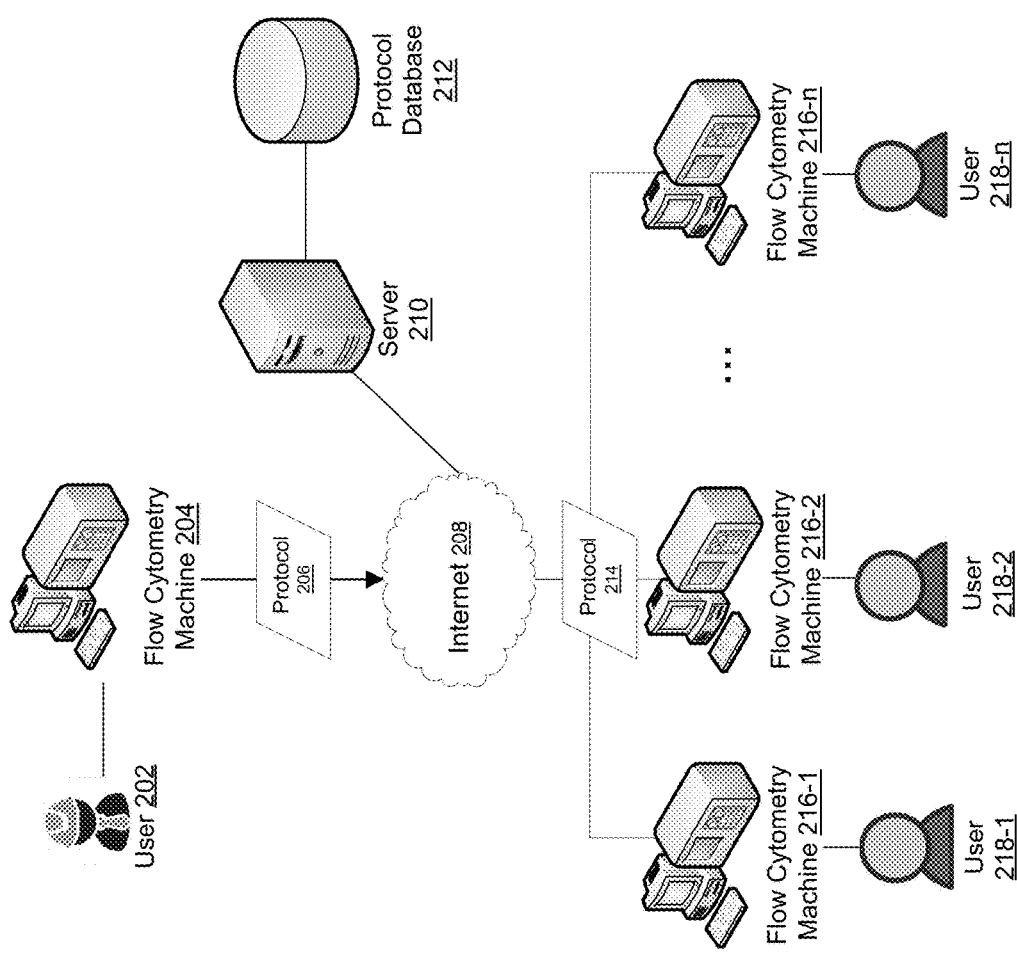
FIG. 2 is a system diagram that illustrates how various flow cytometry machines may utilize a common protocol, in accordance with an example embodiment.

FIG. 2 is a system diagram that illustrates how various flow cytometry machines may utilize a common protocol, in accordance with an example embodiment.

A user 202 may use a flow cytometry machine 204 having various components, such as some of the components shown in FIG. 1. The flow cytometry machine 204 may be configured to provide a visual protocol designer to the user 202, who can use the visual protocol designer to create a graphical representation of a protocol 206. In some embodiments, the system may translate the graphical representation of the protocol 206 into executable code for the protocol 206.

The flow cytometry machine 204 may send the protocol 206 (either as a graphical representation or executable code form) to a server 210 via the Internet 208. The server 210 may further convert the protocol 206 into executable code form if the protocol 206 is not already in executable code form. The server 210 may save the protocol 206 into the protocol database 212 along with other protocols.

There may be one or more flow cytometry machines that will query the server 210 for a specific protocol (or server 210 will disseminate protocols to). These flow cytometry machines are shown in the figure as the flow cytometry machine 216-1 used by the user 218-1, the flow cytometry machine 216-2 used by the user 218-2, and the flow cytometry machine 216-n used by the user 218-n.

For example, the user 218-1 may direct the flow cytometry machine 216-1 to obtain (via the Internet 208) the protocol 214 from the server 210, which may retrieve that protocol from the protocol database 212. In some instances, the protocol 214 may be the same as the protocol 206, but that does not necessarily have to be the case. The flow cytometry machine 216-1 may receive executable code for performing the protocol 214. The flow cytometry machine 216-1 may run the executable code and perform the protocol 214 without the user 218-1 having to input any instructions for the protocol 214.

Figure 3:
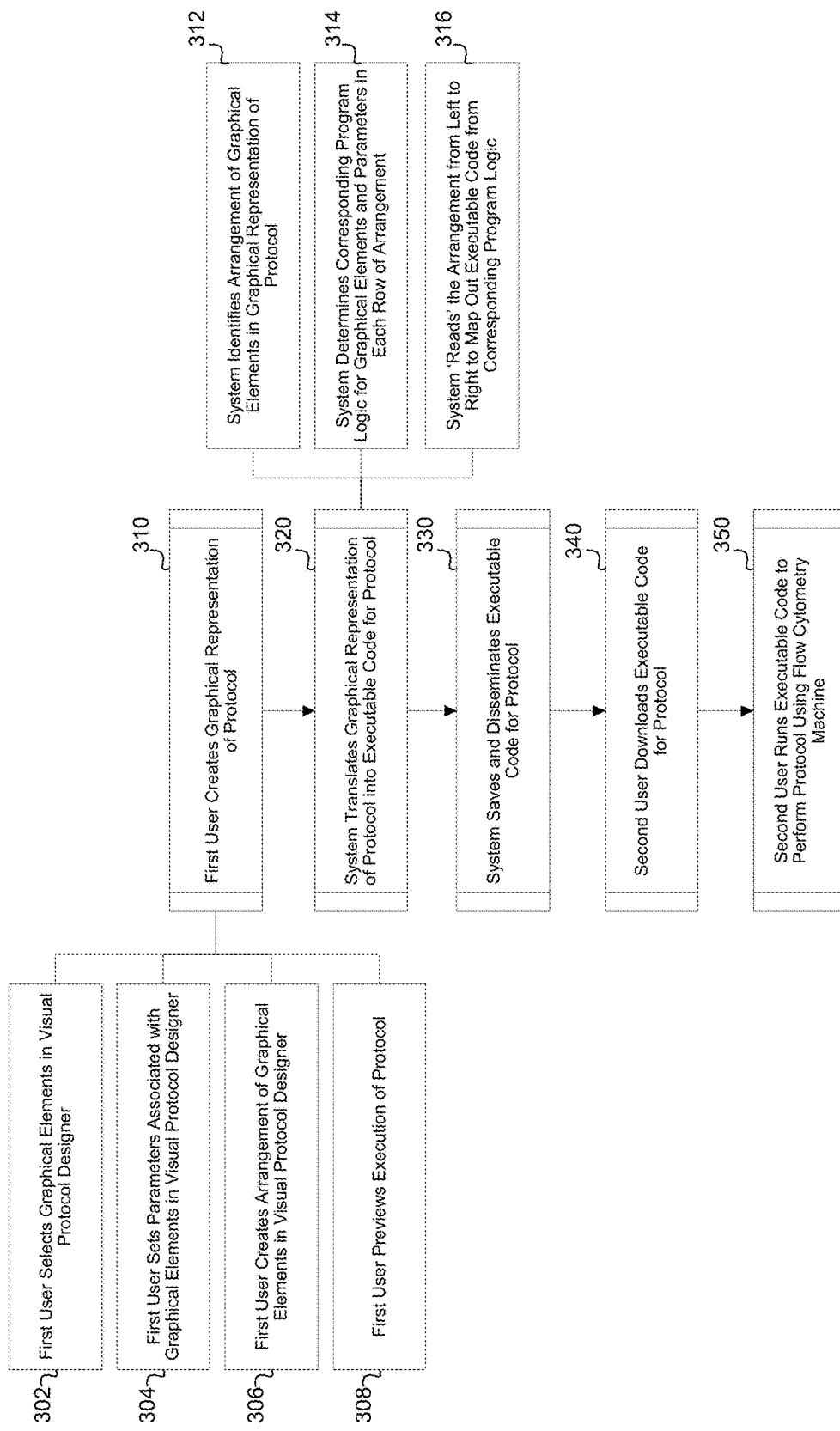
FIG. 3 is a flow diagram that illustrates how a protocol may be generated, disseminated, and used in accordance with some embodiments of the disclosure.

FIG. 3 is a flow diagram that illustrates how a protocol may be generated, disseminated, and used in accordance with some embodiments of the disclosure.

At block 310, a first user may create a graphical representation of a protocol to be performed. The creation of this graphical representation of the protocol may involve multiple sub-blocks or sub-tasks. For instance, in some embodiments the creation of the graphical representation of the protocol may involve block 302, 304, 306, and 308. The various actions associated with blocks 302, 304, 306, and 308 may be performed in various sequences in order to create the graphical representation of the protocol.

At block 302, the first user may select various blocks or graphical elements in a visual protocol designer. The visual protocol designer may be a tool that includes one or more user interfaces that allow the first user to build the graphical representation of a protocol, which will be converted into executable code for the protocol that is usable to control the various components of a flow cytometry machine. Thus, the first user can effectively create a program to instruct a flow cytometry machine to perform a protocol without needing to know how to program. Each of these selected graphical elements may correspond to an aspect of the desired, underlying protocol. For instance, some of the selected graphical elements may be associated with program logic or instructions for a step or task to be performed in the protocol. Some selected graphical elements may be associated with an attribute or parameter for the protocol. Some selected graphical elements may be associated with rules to be followed in the protocol, such as conditional logic for selecting the appropriate step or task to be performed in the protocol. In some embodiments, the user may continue to select graphical elements corresponding to the different aspects of the desired protocol until the entire protocol has been represented among the set of selected graphical elements.

Figure 5:
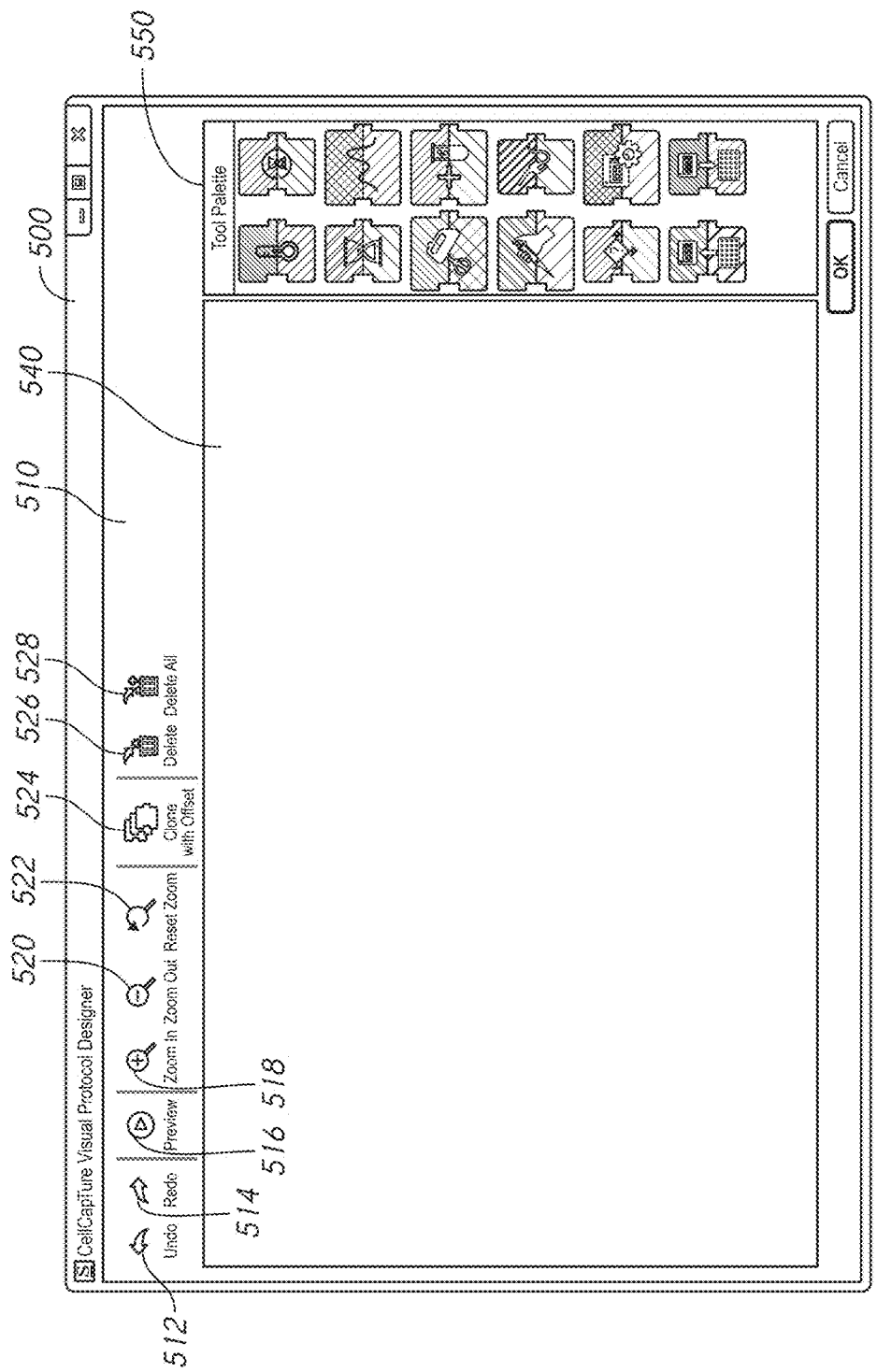
FIG. 5 illustrates an example embodiment of the user interface of a visual protocol designer.
Figure 6:
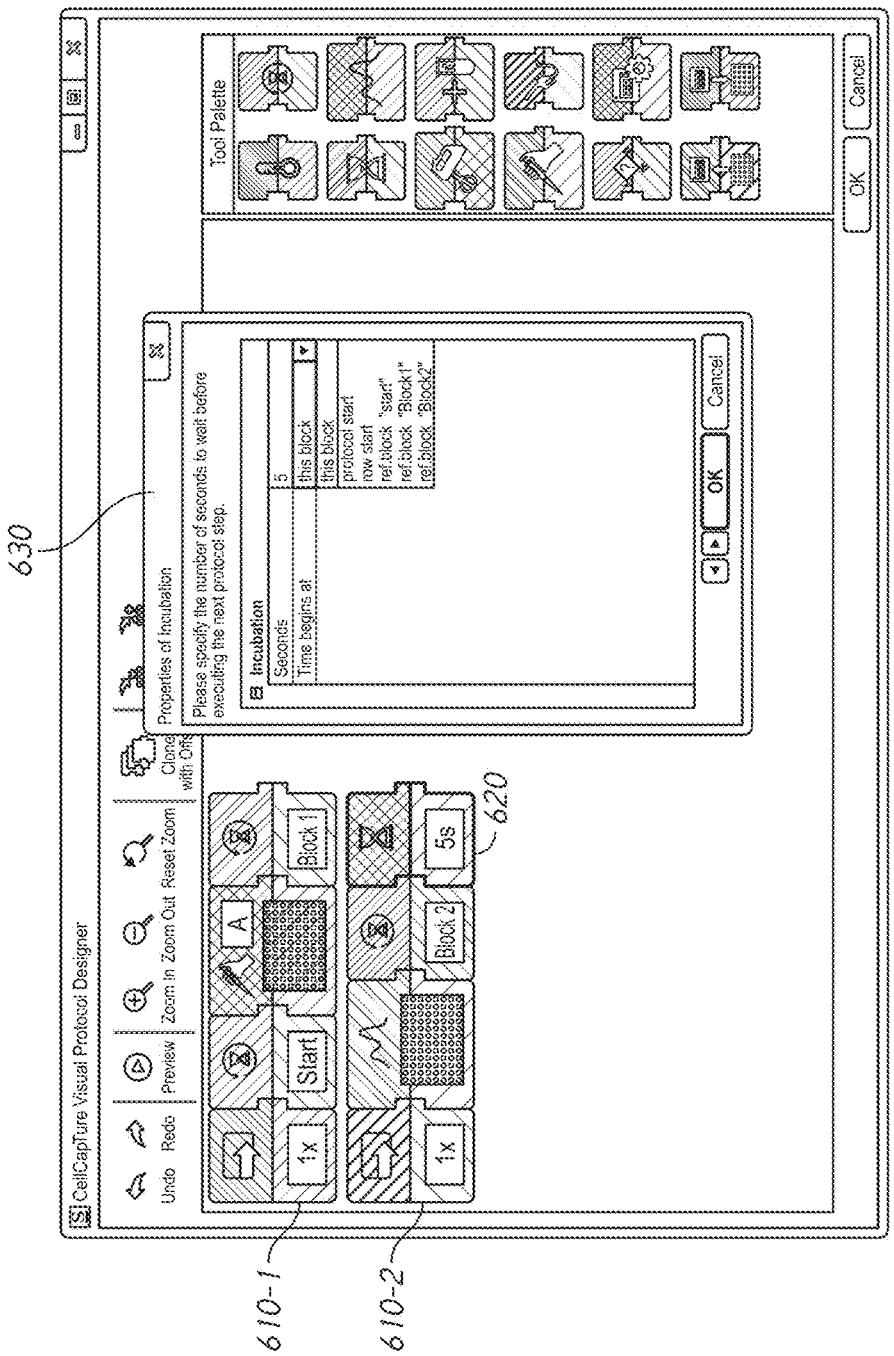
FIG. 6 illustrates an example embodiment of the user interface of a visual protocol designer.

In some embodiments, such as a visual protocol designer having one or more user interfaces similar as shown in FIG. 5 and FIG. 6, a user may select graphical elements from a tool palette or bank of graphical elements. In some embodiments, selecting a graphical element from the bank may involve the user dragging the graphical element from the bank to a workbench, another user interface element that displays the graphical representation of the protocol. Graphical elements within the bank of graphical elements may be individually selected multiple times; a graphical element in the bank may spawn an instance of the graphical element for the graphical representation of the protocol when selected.

Figure 10B:
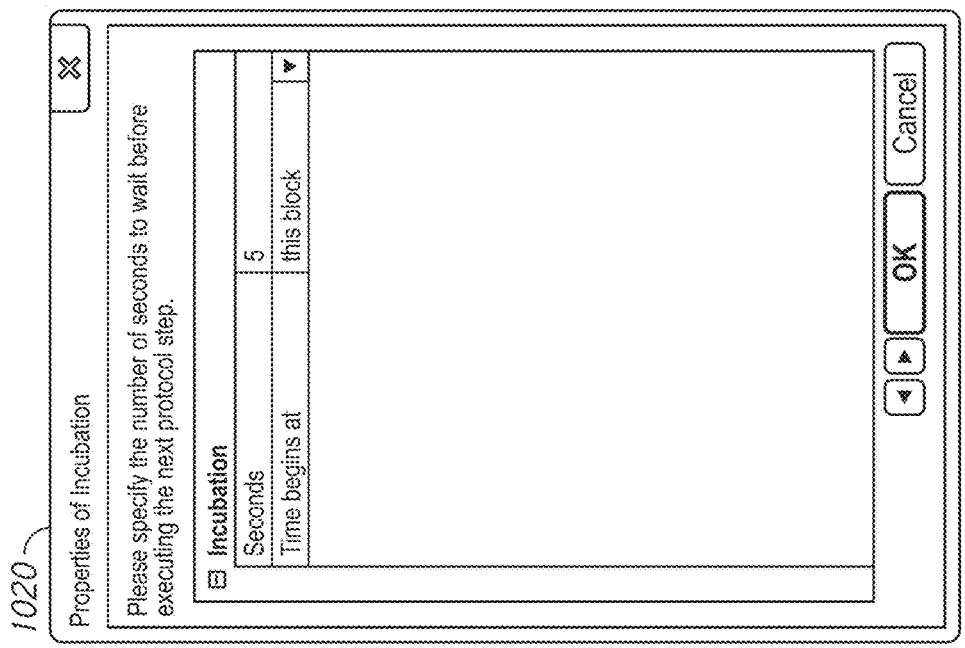
FIG. 10B illustrates an example embodiment of a user interface menu for setting parameters associated with a block.

Referring to FIG. 3, at block 304, the first user may set various parameters associated with each of the graphical elements that were selected in the visual protocol designer. In some embodiments, each graphical element may be associated with a set of parameters, which collectively affect how the instructions associated with the graphical element is carried out. For example, one particular selected graphical element, such as the example graphical element depicted in FIG. 10A, may correspond to a pause or a wait time in the workflow of the protocol during which the components of the flow cytometry machine are instructed to wait for a specified time period before performing another operation in the protocol. Accordingly, the duration of that specified time period could be one of the parameters associated with that particular graphical element that affects how the wait instruction is performed when the protocol is executed. To add to this example, FIG. 10B shows a list of some of the parameters that a user may set for the corresponding wait instruction, which includes a wait time and a starting point for the wait.

Referring to FIG. 3, at block 306, the first user may create an arrangement of the selected graphical elements in the visual protocol designer. For example, the workbench may display all the selected graphical elements in an arrangement. In some embodiments, the user may manipulate and alter the arrangement by moving around the selected graphical elements in the workbench (e.g., through drag-and-drop). As described herein, in some embodiments, the arrangement may include one or more rows of selected graphical elements as shown in FIG. 4 and FIG. 6.

At block 308, the first user may be able to preview an execution of the protocol (e.g., view a simulation of a flow cytometry machine performing the protocol). This preview may be displayed to the user through one or more user interfaces, such as the example user interface shown in FIG. 19. This preview may be based on the arrangement of the selected graphical elements in the graphical representation of the protocol, as well as the set of parameters associated with each of those selected graphical elements. Thus, the preview may be different based on the selected graphical elements, the arrangement that the user places those selected graphical elements in, and how the user configures the set of parameters for each of those selected graphical elements.

In some embodiments, there may be a lock-out or prevention feature for when the first user is building the graphical representation of the protocol. For instance, certain instructions may not be able to be performed by the components of the flow cytometry machine used by the first user. The visual protocol designer may be able to determine the instructions corresponding to the graphical elements that are not able to be performed by the user's flow cytometry machine and prevent the user from selecting those graphical elements, such as by notifying the user or removing/locking those graphical elements in the tool palette. For example, if the user's flow cytometry machine is incapable of performing incubation, the user may not be able to select graphical elements corresponding to incubation to add to the protocol. This feature prevents users from using components (e.g., additional wells/incubators) that are not available or unable to perform the desired instructions of the protocol. In some embodiments, the visual protocol designer may provide a button or embedded link that can be selected by the user in order to purchase the correct components needed to performed the protocol.

At block 320, the system may translate the graphical representation of the protocol into executable code for the protocol (e.g., a form of the protocol that the controller or controller software of the flow cytometry machine can interpret in order to implement the protocol). Additional details for the translation are provided below, as well as in the discussions of FIG. 4 and FIG. 6.

In some embodiments, this translation may be performed by a component of a flow cytometry machine itself, such as by the controller, controller software, or the software providing the graphical user interface of the visual protocol designer. For example, a user could design a protocol and create a graphical representation of the protocol on the computer of the flow cytometry machine, which would then immediately translate the graphical representation of the protocol into executable code. From that point, the protocol could be sent in this executable code form to a server, such as server 210 in FIG. 2 via the Internet 208, where it would be saved in a protocol database 212 for future distribution.

Alternatively, in some other embodiments, the translation may be performed by a server, such as server 210 in FIG. 2. The flow cytometry machine, rather than sending the protocol in the form of executable code, can instead send the graphical representation of the protocol or a file that preserves the graphical representation of the protocol, including how the various graphical elements are arranged. The server can then take the graphical representation of the protocol and translate it into executable code, where it can then be stored in a database such as protocol database 212. There may be certain technical advantages, such as improved compatibility, obtained from performing the translation server-side. For example, the language or the syntax used in the executable code may evolve and change over time as new features are implemented. A flow cytometry machine running an outdated version may translate the graphical representation of the protocol into executable code that may be incompatible with other flow cytometry machines with different software versions. To prevent this problem, the server could perform the translation and be configured to translate the graphical representation of the protocol into varying versions of executable code that are tailored for the varying flow cytometry machines that may seek to perform the protocol. In other words, the server could keep track of the differences between various versions of the software running on different flow cytometry machines and convert the graphical representation of the protocol into executable code that can run on any available flow cytometry machine configuration.

In some embodiments, the translation of the graphical representation of the protocol into executable code may involve multiple sub-blocks or sub-tasks. For instance, the translation of the protocol may involve blocks 312, 314, and 316, which may be performed in various orders and sequences. The translation may be performed by the system which, referred to herein, may include any component of the flow cytometry machine and/or one or more separate computing devices. For example, the system may include the computer 120, as well as central controller 124 and/or the controller software 126, of the flow cytometry machine 100. The system may also include the server 210 and/or the protocol database 212 illustrated in FIG. 2. Any reference to an action performed by the system may be performed by any individual component or set of components within the system.

At block 312, the system may identify, from the graphical representation of the protocol, the arrangement of the graphical elements or icons. For example, if the arrangement includes multiple rows, the system may identify each of the rows in the arrangement, as well as identify the sequence of the graphical elements within each of those rows.

At block 314, the system may determine the corresponding program logic for each of the graphical elements (and the sets of parameters associated with those graphical elements) in each row of the arrangement. For example, the first row of the arrangement may begin with a graphical element for "wait" that is associated with a user-configured wait time parameter of 10 seconds. The system may identify the wait icon and look-up the corresponding program logic for that icon, which could be to pause execution of the protocol by issuing a wait instruction to one or more components of the flow cytometry machine. More specifically, the corresponding program logic in this example would be to issue a wait instruction for 10 seconds based on the wait time parameter. In this manner, the system may identify the corresponding program logic for each graphical element in each row of the arrangement.

At block 316, the system may read the arrangement in some logical order or sequence to map out executable code from the corresponding program logic associated with each graphical element in the arrangement. For example, in an arrangement having multiple rows, the system may map out executable code by first taking the program logic corresponding to the first graphical element of the first row, then the program logic corresponding to the second graphical element of the first row, and so forth until all program logic corresponding to the graphical elements of the first row have been put into the executable code. The system may then move onto the second row and repeat the process for all of the graphical elements in the second row. Then the system would move onto the third row, and so forth, until all of the rows of the arrangement have been mapped into executable code. Further details are provided in FIG. 4.

Accordingly, at block 330, the system may save and disseminate the executable code for the protocol. For example, as shown in FIG. 2, the server 210 may save the executable code for various protocols in a protocol database 212, which may be used to distribute the executable code for the various protocols if users of flow cytometry machines are provided access to the protocol database 212. In some embodiments, the various protocols in the protocol database 212 may be searched or browsed by users of compatible flow cytometry machines. In some embodiments, there may be a web page that lists the various protocols in the protocol database 212 and a user of a flow cytometry machine may be able to navigate the web page to locate a protocol in the protocol database 212 they wish to perform. In other embodiments, the controller software of the user's flow cytometry machine may be configured to directly interface with protocol database 212 and view the various protocols stored within the protocol database 212.

At block 340, a second user may be able to download the executable code for a protocol that the second user wishes to perform. For instance, in certain embodiments, the second user may locate a protocol in the protocol database 212 (via any means, such as through a web browser, through the software running on their flow cytometry machine, and so forth) and download the executable code for the protocol.

At block 350, the second user may run the executable code to perform the protocol on the flow cytometry machine. In some embodiments, the flow cytometry machine may automatically interpret the executable code and carry out the tasks outlined in the protocol without additional guidance being required from the second user.

In some embodiments, there may be a smart protocol feature when the second user attempts to run the executable code for the protocol. For instance, the first user may design the protocol based on what components are available in the flow cytometry machine used by the first user (e.g., flow cytometry machine 204). Not all flow cytometry machines will have those components or be able to perform the functionality of those components. In some cases, the flow cytometry machine for the second user (e.g., flow cytometry machine 216-1) will not be able to execute all the instructions of the protocol. In some embodiments, there may be a smart protocol feature to the system (e.g., part of the software running on the second user's flow cytometry machine) that figures out the components available to the flow cytometry machine, the capabilities of those components. The system may also be able to go through the executable code and determine which additional components would be need to perform the protocol. In some embodiments, the second user would be prompted or notified that the protocol could not be performed. In some embodiments, the second user may be informed regarding which components of the flow cytometry machine are missing or incompatible with the execution of the protocol. In some embodiments, the notification may include a button or embedded link that can be selected by the user in order to purchase the correct components needed to performed the protocol.

FIG. 4 illustrates how a graphical representation of a protocol may be translate into executable code, in accordance with an example embodiment.

The graphical representation 410 of a protocol may have an arrangement of blocks or icons. In some embodiments, the arrangement is displayed to the user through a user interface and the user may be able to change the arrangement by manipulating the blocks displayed in the user interface. In some embodiments, the graphical representation 410 of the protocol may be translated into executable code 420 for the protocol, which may take into consideration the specific icons in the graphical representation 410, the sets of parameters associated with each of those icons, and the arrangement of those icons in the graphical representation 410 of the protocol.

In some embodiments, the arrangement in the graphical representation 410 of a protocol may include one or more rows of blocks or icons, such as the example arrangement shown in FIG. 6. In the figure shown, there is a first row 412-1, a second row 412-2, and a nth row 412-N. In some embodiments, the instructions associated with each of the icons in a row may be interpreted sequentially from left to right during the translation process. For example, the first row 412-1 is shown including, from left to right, icon 1-1, icon 1-2, all the way up to icon 1-N. During the translation process for the first row 412-1, the instructions and set of parameters associated with icon 1-1 may be considered first and mapped into executable code 420 for the protocol. Then the instructions and set of parameters associated with icon 1-2 may be added to the executable code, and so forth until the instructions and set of parameters associated with icon 1-N have been added to the executable code.

In some embodiments, the rows may be considered in the translation process in a manner such that the instructions corresponding to each of the rows of the arrangement may be performed sequentially. For example, the executable code 420 for the protocol may be structured so that after all the instructions corresponding to the icons in row 412-1 have been performed by the flow cytometry machine, the instructions corresponding to the icons in row 412-2 are performed (e.g., the instructions for icon 2-1, then for icon 2-2, until the instructions for icon 2-N have been performed). Thus, the translation may be analogous to reading the words on a page of the book, with rows mapped sequentially (with the icons in each row mapped left-to-right) until the nth row 412-N has been mapped into executable code.

In other embodiments, the rows may be considered in the translation process in a manner such that the instructions corresponding to each of the rows of the arrangement may be performed in parallel. For example, the executable code 420 for the protocol may be structured so that the instructions corresponding to the icons in the first row 412-1 are performed as before (e.g., left to right). However, while the instructions for the first row 412-1 are being performed, the instructions for the second row 412-2 are also performed in parallel if possible.

Thus, the executable code 420 for the protocol will be different as a result of the translation depending on the specific graphical representation 410, which will change based on what icons the user chooses to add to the arrangement, how the user arranges those icons, and what sets of parameters are associated with each of those icons. Each of those icons may correspond to program logic or instructions for the flow cytometry machine, and the translation process may be used to convert each icon into its corresponding program logic (further modified by the position of that icon in the arrangement and its associated set of parameters), which is then added to the executable code 420. Accordingly, executable code 420 for the protocol can be produced by a user without any foundation in programming or knowledge of the programming language the executable code 420 is written in. All the user would need to do is create the graphical representation 410 of the protocol by placing various icons into an arrangement using a user interface, such as the example user interfaces shown in FIG. 5 and FIG. 6.

In some embodiments, the executable code 420 of the protocol may be translated back into the graphical representation 410 of the protocol. In other words, the translation process may not necessarily have to be a one-way function. A user that has the executable code 420 for the protocol (e.g., downloaded it from the internet 208) and wants to make further modifications to the protocol may also be able to do so without needing any programming knowledge. In some embodiments, the executable code 420 may be converted back into a graphical representation 410 by sequentially parsing out each of the instructions in the executable code 420, determining the icon associated with each of those instructions, and generating an arrangement of all of those icons based on their sequence.

In some embodiments, the visual protocol designer may have an optimization feature directed towards identifying improvements that can be made to the structure of the protocol and the graphical representation of the protocol. For example, the visual protocol designer may be able to spot instances where instructions for multiple graphical elements can be combined (e.g., one graphical element can be used in place of two graphical elements in the graphical representation). As a more specific example, there could be a first graphical element corresponding to instructions for mixing and a second graphical element corresponding to instructions for mixing. The visual protocol designer may be able to identify to the user that the instructions for mixing could be combined and tied to a single graphical element in order to improve the efficiency of the protocol.

FIG. 5 illustrates an example embodiment of the user interfaces of a visual protocol designer. More specifically, the figure shows the main user interface 500 of the visual protocol designer, having a toolbar 510, a workbench 540, and a tool palette 550.

In some embodiments, the tool palette 550 may include one or more blocks, or selectable graphical elements that each correspond to program logic or instructions that may be performed by the flow cytometry device. Example embodiments of various blocks and the corresponding program logic are described in conjunction with FIGS. 7A-18B below.

In some embodiments, the blocks from the tool palette 550 may be selected by the user and dragged to the workbench 540. Once blocks are dragged to the workbench 540, those blocks may be positioned and re-arranged by the user to create a graphical representation of a protocol used to perform an experiment with the components of the flow cytometry machine. An example embodiment of the workbench 540 that has been populated with blocks can be seen in FIG. 6. Since each block dragged into the workbench 540 encapsulates or corresponds to limited program logic or instructions, the user may need to utilize multiple blocks in order to piece together the corresponding full set of instructions to be executed in the protocol.

In some embodiments, the workbench 540 may allow for multiple rows of blocks to be arranged and be part of the graphical representation of the protocol. The structure of that arrangement may be preserved when the graphical representation of the protocol is translated into executable code for the protocol. In some embodiments, this may allow for multi-tasking and/or certain instructions to be performed in parallel. For example, the instructions corresponding to two rows of blocks may be performed concurrently. In other embodiments, the instructions corresponding to the rows may be executed sequentially (e.g., the instructions for the first row of blocks may be performed first, and then the instructions for the second row of blocks may be performed afterwards). In some embodiments, the instructions within one row of blocks may be executed sequentially, in an order such as left-to-right. For example, within one row of blocks the instructions for the leftmost block may be performed first, followed by the instructions for the block immediately to the right of it, and so forth until all the instructions corresponding to the blocks in that row have been executed.

In some embodiments, the toolbar 510 may include one or more buttons, such as an undo button 512, a redo button 514, a preview button 516, a zoom in button 518, a zoom out button 520, a reset zoom button 522, a clone with offset button 524, a delete button 526, and a delete all button 528. In some embodiments, the undo button 512 may erase the last change performed within the workbench 540. The undo button 512 may be pressed multiple times to undo older actions. In some embodiments, the redo button 514 may reverse actions that have been undone (e.g., using the undo button 512). The redo button 514 may be pressed multiple times to reverse multiple undo commands.

In some embodiments, the preview button 516 may be used to visually preview or simulate the instructions corresponding to the current arrangement of blocks in workbench 540, allowing a user to see the affected wells corresponding to the instructions for each block in the graphical representation of the protocol. An example embodiment of this preview feature is shown and further described in regards to FIG. 19.

In some embodiments, the zoom in button 518 may be pressed to zoom in further into the workbench 540. In some embodiments, the zoom out button 520 may be pressed to zoom out from a portion of the workbench 540 to display a larger area of the workbench 540. In some embodiments, the reset zoom button 522 may be used to zoom out such that the whole area of the workbench 540 is viewable in one-click.

In some embodiments, the clone with offset button 524 may be used to create a copy of the selected block(s) in the workbench 540. The copy may be placed in another row of the arrangement based on its offset. For example, clicking on the clone with offset button 524 may open up a menu that allows a user to specify a column offset for the blocks being copied, a row offset for the blocks being copied, and a number of copies to create. The column and row offsets may be applied to the affected wells of each iterative copy created. In other words, if the user specified a column offset of 1, a row offset of 1, and to create 7 copies of a selected row of blocks, there would be 11 copies of the selected blocks created with each copy occupying its own row (e.g., 11 rows of blocks would be added). Starting from the first copy, the offsets would be applied to the affected wells of each subsequent copy. For example, the second copy would have the affected wells of the blocks shifted down a row and over a column. The next copy would have the affected wells of the blocks shifted down another row and over another column. In some embodiments, the offset may only affect blocks directed to record, mixing, reagent adding, and well-to-well pipetting. Example embodiments of various blocks are described with additional details in FIGS. 7A-18B.

In some embodiments, the delete button 526 may be used to delete a selected block in the workbench 540. In some embodiments, the delete all button 528 may be used to delete all of the blocks in the workbench 540. In some of such embodiments, a prompt may request the user's confirmation to delete all the blocks in order to avoid the user accidentally deleting all the blocks.

FIG. 6 illustrates an example embodiment of the user interfaces of a visual protocol designer. More specifically, the figure shows similar user interfaces as those shown in FIG. 5. However, the workbench 540 has been populated with two rows of blocks: a first row 610-1 and a second row 610-2.

The first row 610-1 contains four blocks arranged from left-to-right. The first block is a row execution count block (e.g., as in FIG. 7A) with a parameter state display of "1x". The second block is a reference block (e.g., as in FIG. 9A) with a parameter state display of "Start". The third block is a well-to-well pipetting block (e.g., as in FIG. 14A) with a parameter state display showing no wells affected. The fourth block is another reference block with a parameter display of "Block 1" (e.g., as in FIG. 9A).

The second row 610-2 also contains four blocks arranged from left-to-right. The first block is a row execution count block (e.g., as in FIG. 7A) with a parameter state display of "lx". The second block is a record block (e.g., as in FIG. 11A) with a parameter state display of no wells affected. The third block is a reference block (e.g., as in FIG. 9A) with a parameter state display of "Block 2". The fourth block is an incubation block with a parameter state display of "5 s" (e.g., as in FIG. 10A).

In some embodiments, the arrangement of blocks within each row may dictate how instructions corresponding to that arrangement are translated into executable code. For example, for the first row 610-1 the first block corresponds to instructions that the row is to be executed only once, which can be translated into executable code and/or a structure for that code (e.g., no loops). The second block in the first 610-1 corresponds to a reference point named "Start", which can be inserted to the executable code. In some embodiments, the "Start" reference point may simply be a comment in the un-compiled code for the purposes of the translation. For a later block that utilizes that reference point (e.g., instructing to begin a timer at the "Start" reference point), that instruction can be inserted at the "Start" reference point in the executable code. The third block in the row corresponds to instructions to initiate well-to-well pipetting, which can be added to the code to be performed sequentially after the instructions from the previous blocks.

As shown in the figure, the fourth block in the second row 610-2 (the incubation block) is the selected block 620, which creates a highlight or outline of the block within the workbench 540 to signify to the user that the block is selected. In some embodiments, the user may modify a set of parameters, properties, or options associated with the selected block 620. For example, there may be a menu 630 that allows the user to modify the parameters associated with the selected block 620. As seen in the figure, the user can select the number of seconds to wait (e.g., perform incubation) for the instructions tied to the incubation block that is the selected block 620. The user may also specify a reference point at which the waiting begins. For instance, the dropdown in menu 630 shows available options for the current block, the start of the protocol, the start of the row, the "Start" reference block, the "Block 1" reference block, and the "Block 2" reference block. For example, if the user selected the "Start" reference block as the point at which the waiting begins, during translation of this graphical representation of the protocol into executable code, the command to begin waiting would be inserted at the "Start" reference point in the code (which was previously added when translating the "Start" reference block).

Figure 7A:
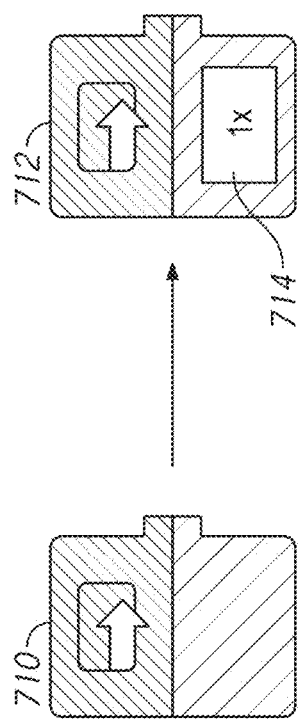
FIG. 7A illustrates an example embodiment of a block that a user may use in a graphical representation of a protocol.
Figure 7B:
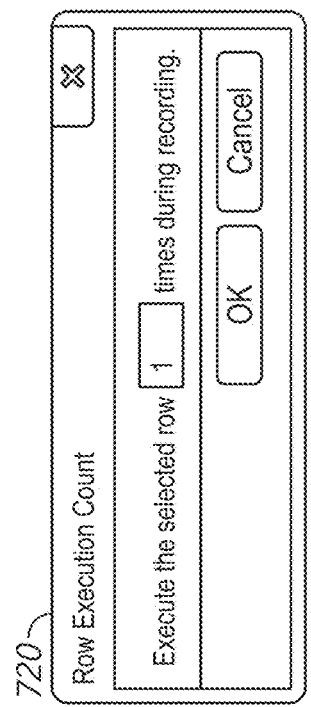
FIG. 7B illustrates an example embodiment of a user interface menu for setting parameters associated with a block.

FIG. 7A illustrates an example embodiment of a row execution count block that a user may use in a graphical representation of a protocol. FIG. 7B illustrates an example embodiment of a properties menu associated with the row execution count block.

More specifically, FIG. 7A illustrates an example embodiment of a row execution count block 710. In some embodiments, block 710 is a selectable graphical element within the visual protocol designer that corresponds to the number of times to repeat a row of instructions encapsulated in the protocol. In other word, block 710 may be used to set the number of repetitions for the instructions corresponding to a row of blocks within the graphical representation of the protocol. In some embodiments, block 710 may be automatically generated and placed in a row of the arrangement if there is at least one other block from the tool palette that was moved into that row.

In some embodiments, the row execution count block 710 displayed in the user interface of the visual protocol designer may change or update to block 712 once the user sets the properties or parameters associated with block 710, such as through menu 720 shown in FIG. 7B. In some embodiments, the menu 720 allows a user to specify the number of times to execute the row associated with the row execution count block 710. Once that parameter associated with row execution count block 710 is set by the user, the row execution count block 710 displayed in the user interface may update to block 712 and show the state of the parameter set by the user. For instance, if the user sets the row execution count parameter to "1" for the row execution count block 710, such that the row associated with the row execution count block 710 is executed only once (e.g., the row is not looped), block 710 may be visually updated in the user interface to block 712 having a parameter state display 714. As seen in the figure, the parameter state display 714 shows "1X" which may indicate to the user that the row execution count is set to 1. In some embodiments, the parameter state display 714 may be configured to display other parameters associated with the block such that the user can quickly see those parameters without having to open the menu 720.

Figure 8B:
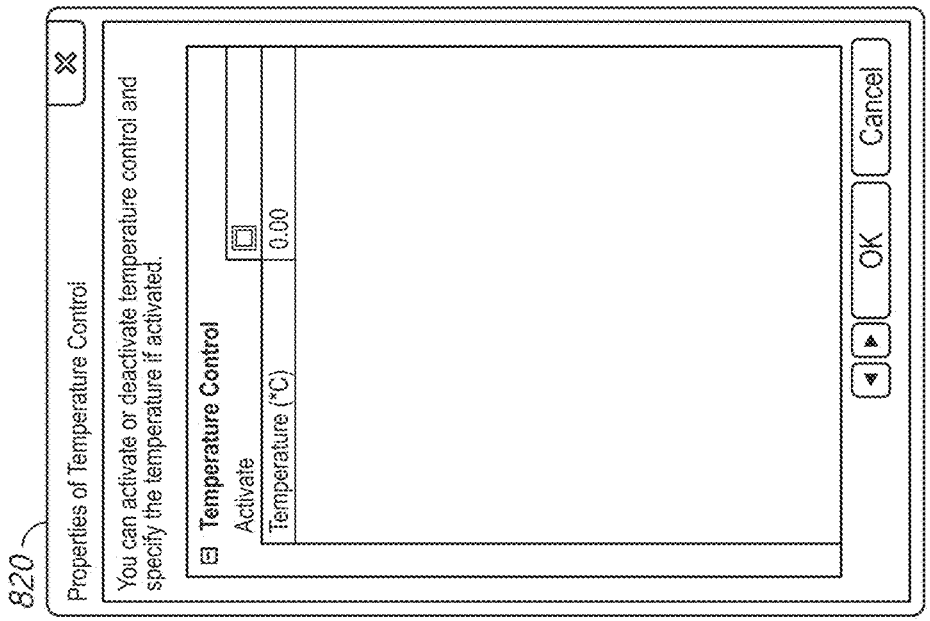
FIG. 8B illustrates an example embodiment of a user interface menu for setting parameters associated with a block.
Figure 8A:
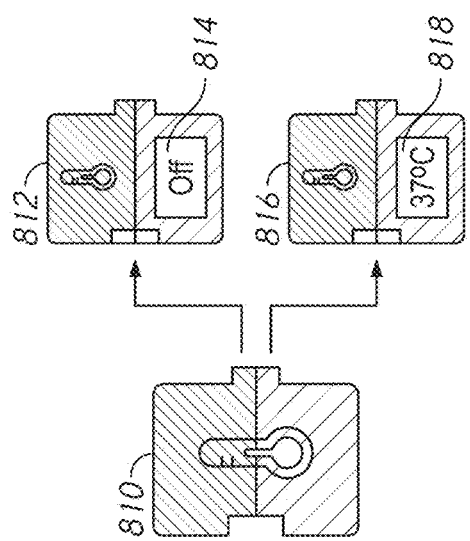
FIG. 8A illustrates an example embodiment of a block that a user may use in a graphical representation of a protocol.

FIG. 8A illustrates an example embodiment of a temperature control block that a user may use in a graphical representation of a protocol. FIG. 8B illustrates an example embodiment of a properties menu associated with the temperature control block.

More specifically, FIG. 8A illustrates an example embodiment of a temperature control block 810. In some embodiments, block 810 is a selectable graphical element within the visual protocol designer that corresponds to the temperature setting for one or more components of the flow cytometry machine (or accessory devices to be used with the flow cytometry machine) during the execution of the protocol. In other words, block 810 may be used to set the temperature of a temperature control module of one or more components of the flow cytometry machine, such as an incubator, autosampler, plate loader, automatic liquid handler, and so forth.

In some embodiments, the temperature control block 810 displayed in the user interface of the visual protocol designer may change or update once the user sets the properties or parameters associated with block 810, such as through menu 820 shown in FIG. 8B. In some embodiments, the menu 820 allows a user to specify whether to activate or deactivate the temperature control. As shown in FIG. 8B, the menu 820 includes a checkbox for activation. When the checkbox is unchecked, the temperature control is deactivated; when the checkbox is checked, the temperature control is activated and the temperature field is unlocked. In some embodiments, the temperature field allows the user to set the desired temperature to be maintained by the temperature control module within one or more components of the flow cytometry machine. In some embodiments, the user may set the temperature in the temperature field in the Celsius scale. In some of such embodiments, there may be limited temperature range for the temperature (e.g., the user may be limited to setting a temperature between 8° C.-37° C.).

In some embodiments, once the parameters associated with the temperature control block 810 are set by the user, the temperature control block 810 displayed in the user interface may update to show the state of the parameters set by the user. For instance, if the user deactivates the temperature control within the menu 820 (e.g., the activation checkbox is unchecked), block 810 may be visually updated in the user interface to block 812 having a parameter state display 814. As seen in the figure, the parameter state display 814 shows "Off" which may indicate to the user that the temperature control is deactivated. Alternatively, if the user activates the temperature control within the menu 820 and sets the temperature (e.g., to 37° C.), block 810 may be visually updated to block 816 having a parameter state display 818. As seen in the figure, the parameter state display 818 shows "37° C." which may indicate to the user that the temperature control is activated and the temperature level is set to 37° C.

Figure 9B:
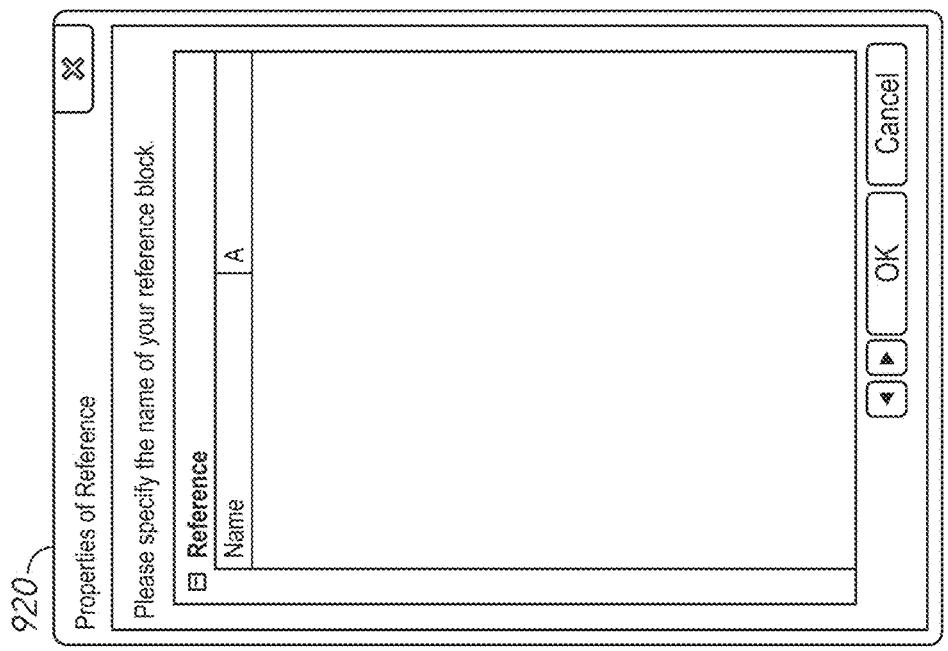
FIG. 9B illustrates an example embodiment of a user interface menu for setting parameters associated with a block.
Figure 9A:
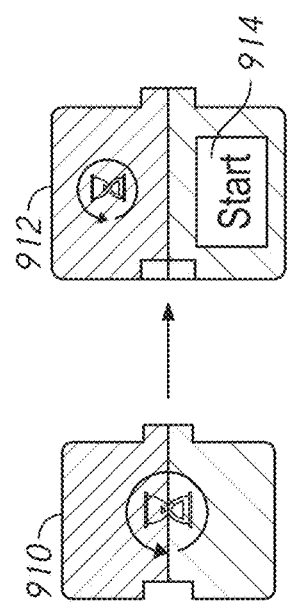
FIG. 9A illustrates an example embodiment of a block that a user may use in a graphical representation of a protocol.

FIG. 9A illustrates an example embodiment of a reference block that a user may use in a graphical representation of a protocol. FIG. 9B illustrates an example embodiment of a properties menu associated with the reference block.

More specifically, FIG. 9A illustrates an example embodiment of a reference block 910. In some embodiments, block 910 is a selectable graphical element within the visual protocol designer that a user may designate as a reference point within the protocol that other blocks may be configured to refer to. For example, the user may configure other blocks to start or end at a specific point in the protocol represented by block 910. As a more specific example, a user may select an incubation block and configure it such that incubation begins at a specific point in the protocol designed by a reference block 910. Conceptually, this may be understood as similar to the use of pointers or GOTO statements in programming.

In some embodiments, the reference block 910 displayed in the user interface of the visual protocol designer may change or update once the user sets the properties or parameters associated with block 910, such as through menu 920 shown in FIG. 9B. In some embodiments, the menu 920 allows a user to specify a reference name to associate with the reference block 910 in a text field. For example, FIG. 9B illustrates a menu 920 where "A" is set as the name of the reference block 910.

In some embodiments, once the parameters associated with the reference block 910 are set by the user, the reference block 910 displayed in the user interface may update to show the state of the parameters set by the user. For instance, if the user sets the name of the reference block within the menu 920 (e.g., the activation checkbox is unchecked), block 910 may be visually updated in the user interface to block 912 having a parameter state display 914. As seen in the figure, the parameter state display 914 shows "Start" which may indicate to the user that the name of the block has been set to "Start". In some embodiments, this name of the block may be selectable as a reference point when configuring other blocks (e.g., "Start" may be selectable as a reference point when configuring other blocks, such as when to begin incubation).

Figure 10A:
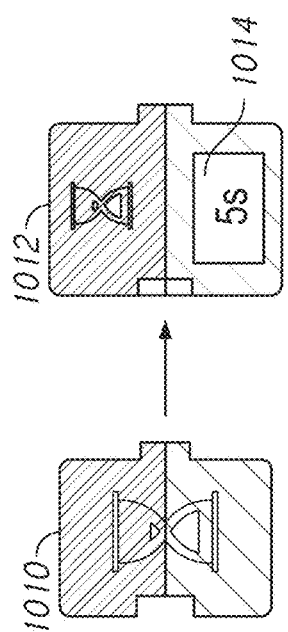
FIG. 10A illustrates an example embodiment of a block that a user may use in a graphical representation of a protocol.

FIG. 10A illustrates an example embodiment of an incubation block that a user may use in a graphical representation of a protocol. FIG. 10B illustrates an example embodiment of a properties menu associated with the incubation block.

More specifically, FIG. 10A illustrates an example embodiment of an incubation block 1010. In some embodiments, block 1010 is a selectable graphical element within the visual protocol designer that corresponds to instructing the flow cytometry machine to incubate a plate for a specified period of time.

In some embodiments, the incubation block 1010 displayed in the user interface of the visual protocol designer may change or update once the user sets the properties or parameters associated with block 1010, such as through menu 1020 shown in FIG. 10B. In some embodiments, the menu 1020 allows a user to specify a duration of the time for the incubation. In some of such embodiments, the user may specify the duration of the incubation in seconds. In some of such embodiments, the set duration may be limited to a certain range, such as 0-86400 seconds. In some embodiments, the menu 1020 also allows a user to set a point in the protocol at which the incubation time period begins.

In some embodiments, once the parameters associated with the incubation block 1010 are set by the user, the incubation block 1010 displayed in the user interface may update to show the state of the parameters set by the user. For instance, if the user sets the incubation duration to 5 seconds in the menu 1020, block 1010 may be visually updated in the user interface to block 1012 having a parameter state display 1014. As seen in the figure, the parameter state display 1014 shows "5 s" which may indicate to the user that the incubation duration is set to 5 seconds.

Figure 11B:
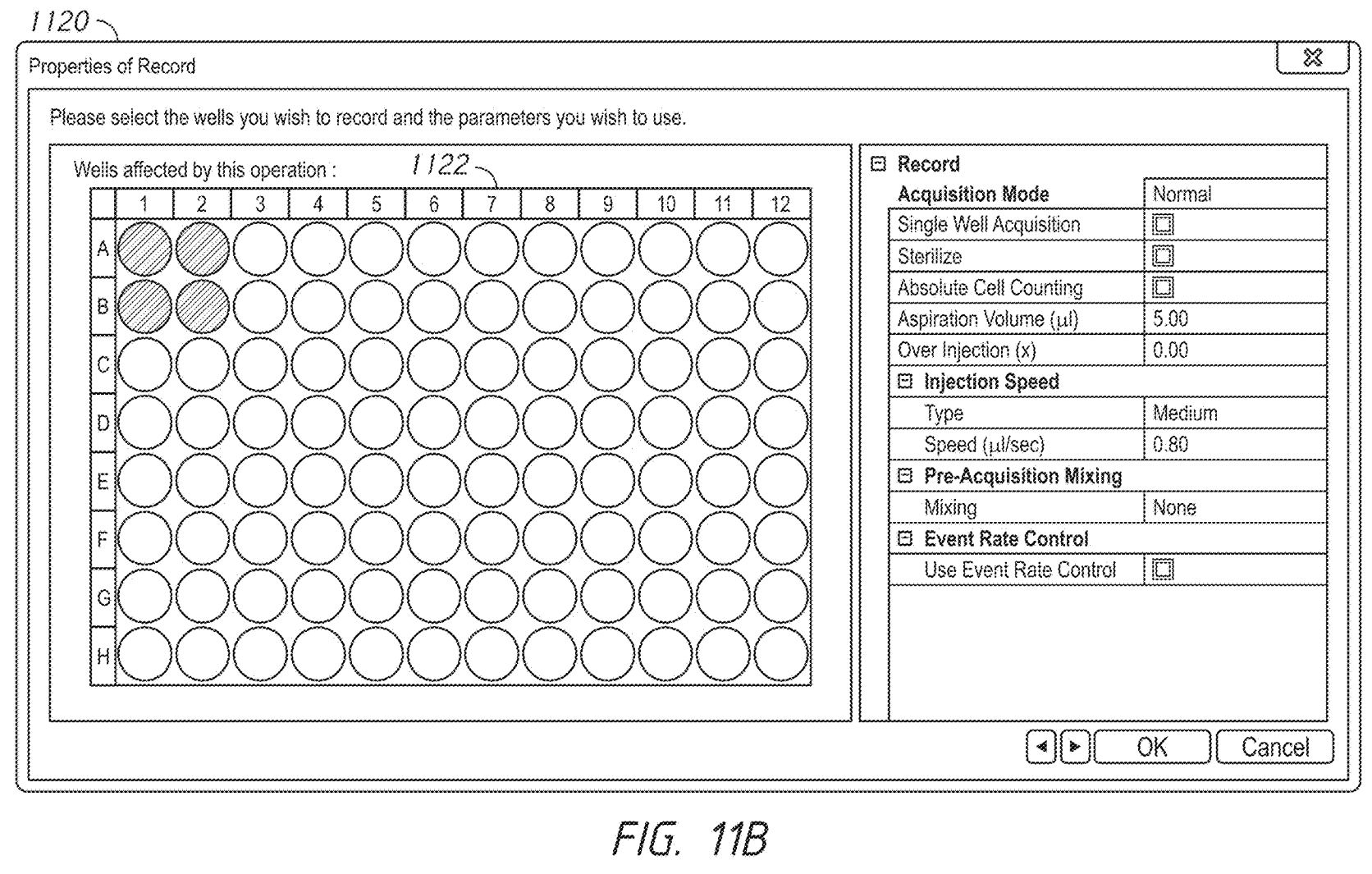

FIG. 11A illustrates an example embodiment of a record block that a user may use in a graphical representation of a protocol. FIG. 11B illustrates an example embodiment of a properties menu associated with the record block.

More specifically, FIG. 11A illustrates an example embodiment of a record block 1110. In some embodiments, block 1110 is a selectable graphical element within the visual protocol designer that a user may use to record selected wells on the plate.

In some embodiments, the record block 1110 displayed in the user interface of the visual protocol designer may change or update once the user sets the properties or parameters associated with block 1110, such as through menu 1120 shown in FIG. 11B. In some embodiments, the menu 1120 allows a user to specify properties such as the wells affected by the operation, acquisition mode, single well acquisition, sterilize, absolute cell counting, aspiration volume, over injection, injection speed, and type, whether to perform pre-acquisition mixing, and whether to use event rate control. In some embodiments, the menu 1120 may include a well selector 1122, which may display a representation of all the wells in a plate. For example, FIG. 11B shows a 8×12 well plate having a total of 96 wells. The user may be able to highlight and select individual wells in the well selector 1122; selecting a well of the plate shown in the well selector 1122 may outline that well or change that well to a different color in order to indicate to the user that the well has been selected and is affected by the operation. The record operation of the protocol associated with the record block 1110 may be performed on the user-selected wells of the plate.

In some embodiments, the acquisition mode parameter may have various settings. The normal setting may be the default setting that is appropriate for most cases, and that setting may enable auto-backflush and utilize average wash times. The high throughput setting may increase syringe speed while allowing some possible carryover, skipping auto-backflush and utilizing fast wash times. The low carryover setting may take extra time in order to minimize carryover between wells, and that setting may enable auto-backflush and utilize longer wash times with a slower syringe speed.

In some embodiments, checking the single well acquisition checkbox may aspirate the sample with one probe at a time in order to minimize the time the samples are inside the probes prior to injection. In some embodiments, checking the sterilize checkbox may sterilize each probe and/or rinse them with fluid in order to avoid biological contamination between wells. In some embodiments, checking the absolute cell counting checkbox allows a user to perform precise volumetric cell count measurements. In some embodiments, the aspiration volume field allows the user to set a sample volume (in μL) to be used from the well from aspiration. In some of such embodiments, there may be a limited range for the aspiration volume field, such as between 5-400 μL. In some embodiments, the over injection field allows the user to inject extra sheath fluid, measured in multiples of the aspiration volume, into the sample line after the full sample volume has been injected. Injecting the extra sheath fluid may minimize carryover between wells and also insure the acquisition of the full aspiration volume. In some embodiments, there may be a limited range for the over injection field, such as a multiplier between 0 and 6 times the aspiration volume.

In some embodiments, the injection speed type may be chosen from high, medium, low, and custom injection speeds. If custom injection speed is selected, the field for injection speed may unlock to allow the user to specify a custom injection speed in μL/sec. In some embodiments, there may be a limited range for the custom injection speed, such as between 0.1 and 2 μL/sec.

In some embodiments, the pre-acquisition mixing parameter may be chosen from none, low, high, and custom. In some embodiments, checking the use event rate control checkbox may control the sample injection speed to achieve a specified event rate per second during the acquisition based on the actual sample concentration. The user can set a target event rate, and the injection speed will be modified to achieve the desired event rate.

In some embodiments, once the parameters associated with the record block 1110 are set by the user, the record block 1110 displayed in the user interface may update to show the state of the parameters set by the user. For instance, if the user selects specific wells within the well selector 1122 of the menu 1120, block 1110 may be visually updated in the user interface to block 1112 having a parameter state display 1114. As seen in the figure, the parameter state display 1114 shows a representation of the user-selected wells in the plate, which are the wells affected by the corresponding operation. The user may be able to quickly glance at the block 1112 in the user interface in order to determine the selected wells without having to open the menu 1120. (This also stands true for mixing, reagent adding, and well-to-well pipetting blocks).

Figure 12A:
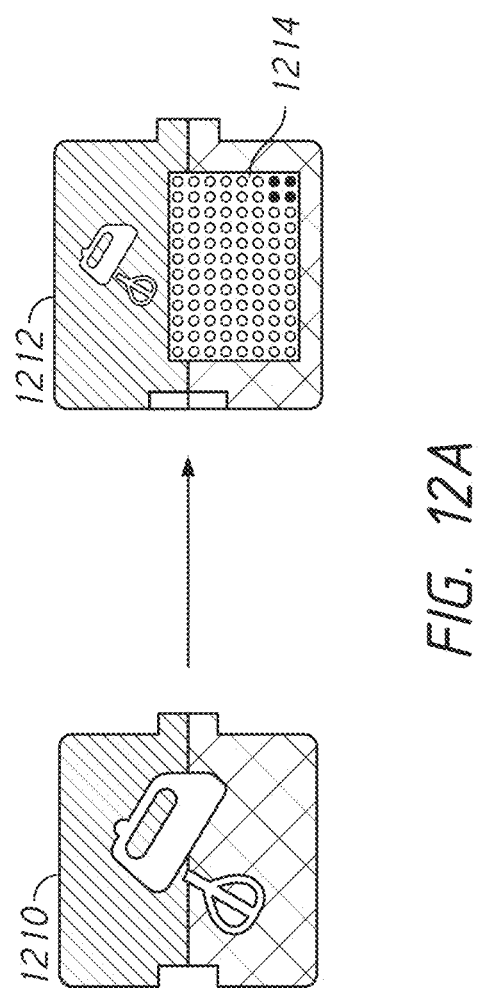
FIG. 12A illustrates an example embodiment of a block that a user may use in a graphical representation of a protocol.
Figure 12B:
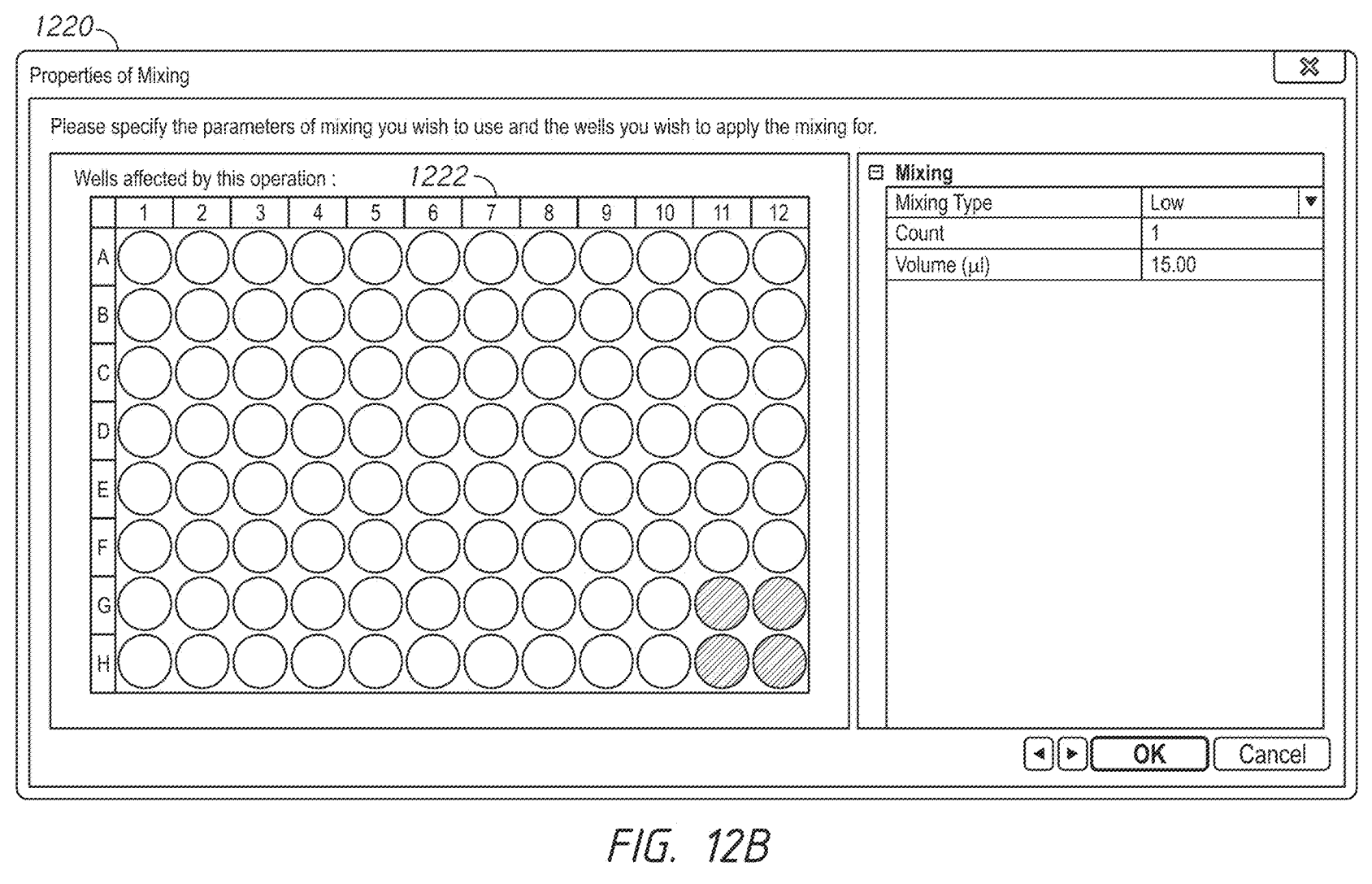

FIG. 12A illustrates an example embodiment of a mixing block that a user may use in a graphical representation of a protocol. FIG. 12B illustrates an example embodiment of a properties menu associated with the mixing block.

More specifically, FIG. 12A illustrates an example embodiment of a mixing block 1210. In some embodiments, block 1210 is a selectable graphical element within the visual protocol designer that a user may use to mix the samples within selected wells of a plate.

In some embodiments, the mixing block 1210 displayed in the user interface of the visual protocol designer may change or update once the user sets the properties or parameters associated with block 1210, such as through menu 1220 shown in FIG. 12B. In some embodiments, the menu 1220 allows a user to specify properties such as the wells affected by the operation, mixing type, count, and volume. In some embodiments, for the mixing type property the user may be able to choose from low, high, or custom options. In some embodiments, the user may be able to set the count property if the mixing type is set to custom. In some of such embodiments, the custom count may be between 1-10. In some embodiments, the user may be able to set the volume property if the mixing type is set to custom. In some embodiments, the custom volume may be between 5-75 μL.

In some embodiments, the menu 1220 may include a well selector 1222, which may display a representation of all the wells in a plate. For example, FIG. 12B shows a 8×12 well plate having a total of 96 wells. The user may be able to highlight and select individual wells in the well selector 1222; selecting a well of the plate shown in the well selector 1222 may outline that well or change that well to a different color in order to indicate to the user that the well has been selected. The mixing operation of the protocol associated with the mixing block 1210 may be performed on the user-selected wells of the plate; selected wells of the plate may have the sample contained in those wells mixed.

In some embodiments, once the parameters associated with the mixing block 1210 are set by the user, the mixing block 1210 displayed in the user interface may update to show the state of the parameters set by the user. For instance, if the user selects specific wells within the well selector 1222 of the menu 1220, block 1210 may be visually updated in the user interface to block 1212 having a parameter state display 1214. As seen in FIG. 12A, the parameter state display 1214 shows a representation of the user-selected wells in the plate. The user may be able to quickly glance at the block 1212 in the user interface in order to determine the selected wells without having to open the menu 1220 of FIG. 12B.

Figure 13A:
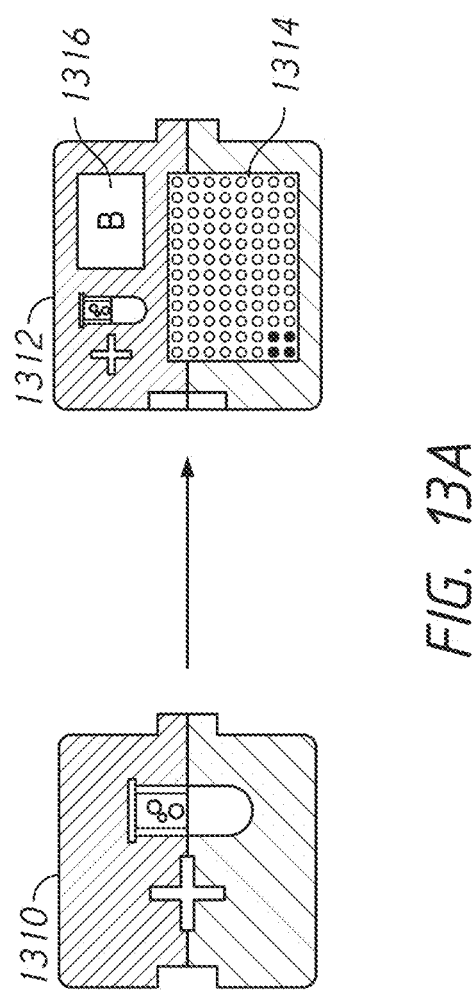
FIG. 13A illustrates an example embodiment of a block that a user may use in a graphical representation of a protocol.
Figure 13B:
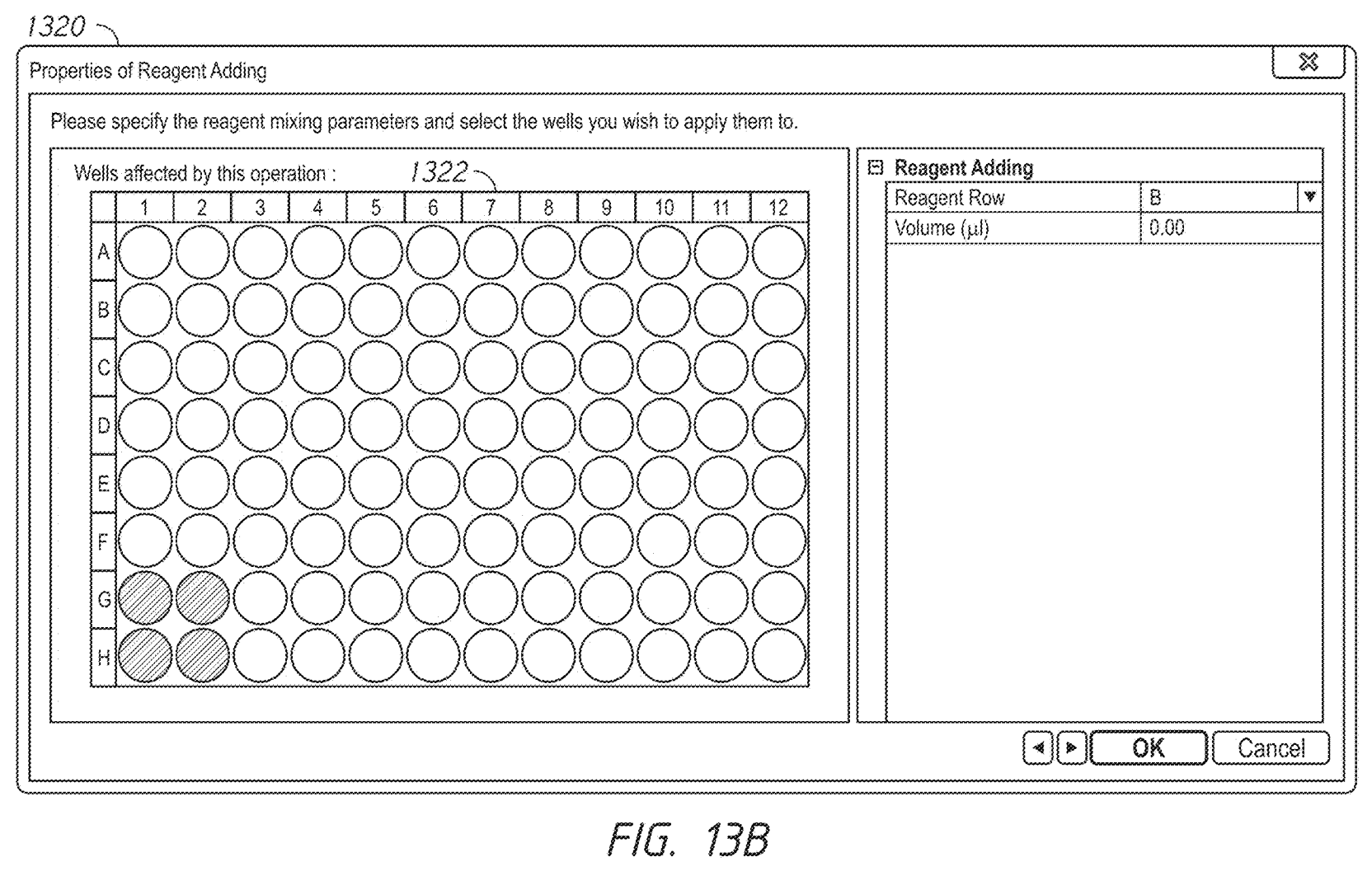

FIG. 13A illustrates an example embodiment of a reagent adding block that a user may use in a graphical representation of a protocol. FIG. 13B illustrates an example embodiment of a properties menu associated with the reagent adding block.

More specifically, FIG. 13A illustrates an example embodiment of a reagent adding block 1310. In some embodiments, block 1310 is a selectable graphical element within the visual protocol designer that a user may use to add reagent to selected wells of a plate. More specifically, the reagent adding block may be used to add reagent to the selected wells from the Eppendorf tubes located in holder next to the plate within one or more components of the flow cytometry machine.

In some embodiments, the reagent adding block 1310 displayed in the user interface of the visual protocol designer may change or update once the user sets the properties or parameters associated with block 1310, such as through menu 1320 shown in FIG. 13B. In some embodiments, the menu 1320 allows a user to specify properties such as the wells affected by the operation, reagent row, and the reagent volume. In some embodiments, for the reagent row the user may be able to select the desired reagent row that contains the reagent to be added. In some embodiments, the user may be able to set the reagent volume, which is the volume of the reagent to be added in μL.

In some embodiments, the menu 1320 may include a well selector 1322, which may display a representation of all the wells in a plate. For example, FIG. 13B shows a 8×12 well plate having a total of 96 wells. The user may be able to highlight and select individual wells in the well selector 1322; selecting a well of the plate shown in the well selector 1322 may outline that well or change that well to a different color in order to indicate to the user that the well has been selected. The reagent addition operation of the protocol associated with the reagent adding block 1310 may be performed on the user-selected wells of the plate; selected wells of the plate may have reagent added to them from the Eppendorf tubes.

In some embodiments, once the parameters associated with the reagent adding block 1310 are set by the user, the reagent adding block 1310 displayed in the user interface may update to show the state of the parameters set by the user. For instance, if the user selects specific wells within the well selector 1322 of the menu 1320, block 1310 may be visually updated in the user interface to block 1312 having a parameter state display 1314 and/or the parameter state display 1316. As seen in FIG. 13A, the parameter state display 1314 shows a representation of the user-selected wells in the plate. The user may be able to quickly glance at the block 1312 in the user interface in order to determine the selected wells without having to open the menu 1320 of FIG. 13B. The parameter state display 1316 shows the reagent row property; as seen in the figure, the parameter state display 1316 shows "B" which indicates the reagent row from which reagent is to be added to the selected wells.

Figure 14A:
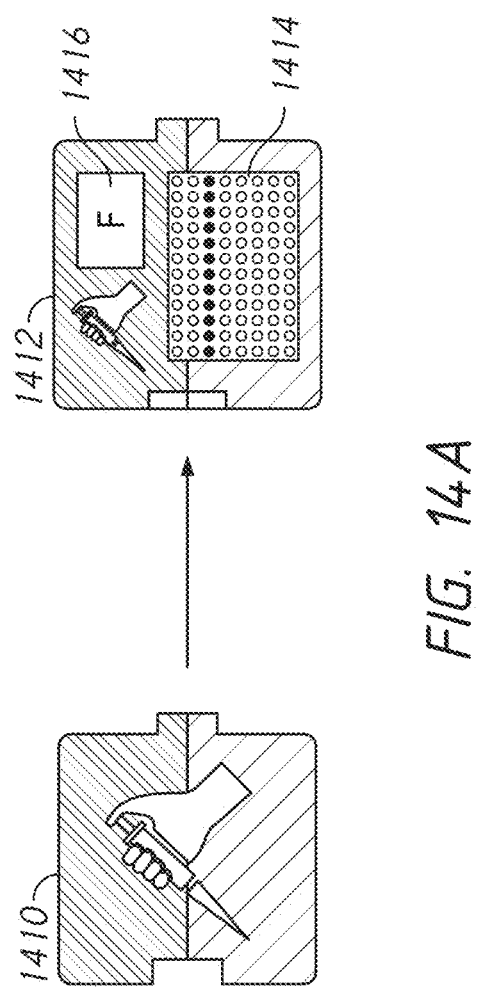
FIG. 14A illustrates an example embodiment of a block that a user may use in a graphical representation of a protocol.
Figure 14B:
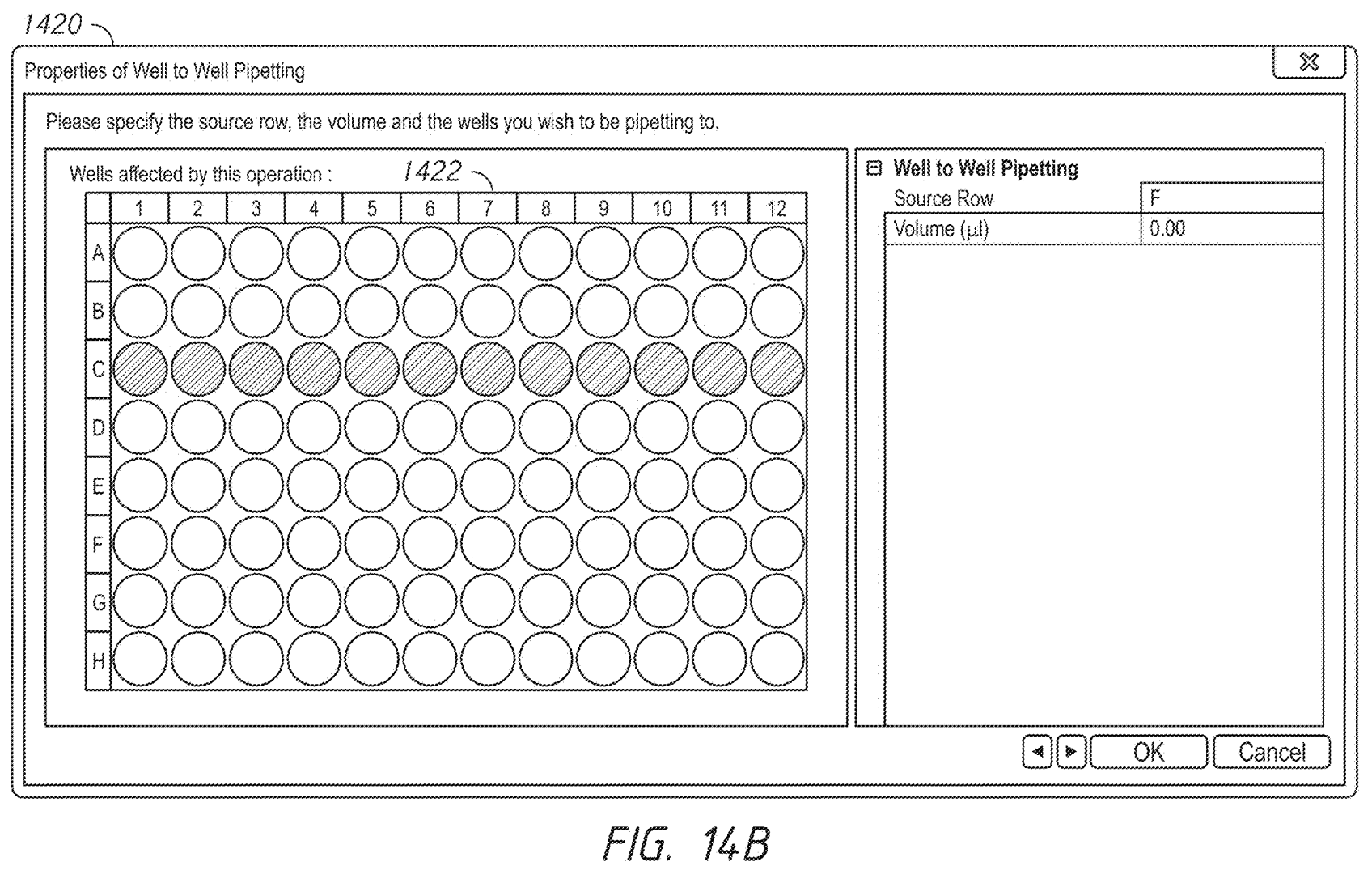

FIG. 14A illustrates an example embodiment of a well-to-well pipetting block that a user may use in a graphical representation of a protocol. FIG. 14B illustrates an example embodiment of a properties menu associated with the well-to-well pipetting block.

More specifically, FIG. 14A illustrates an example embodiment of a well-to-well pipetting block 1410. In some embodiments, block 1410 is a selectable graphical element within the visual protocol designer that a user may use to pipette sample between rows on the same column of the plate. For example, the sample in a well in position A5 (e.g., row 1, column 5) can be pipetted to/from wells B5-H5 (e.g., rows 2-8, column 5).

In some embodiments, the well-to-well pipetting block 1410 displayed in the user interface of the visual protocol designer may change or update once the user sets the properties or parameters associated with block 1410, such as through menu 1420 shown in FIG. 14B. In some embodiments, the menu 1420 allows a user to specify properties such as the wells affected by the operation, source row, and the source volume. In some embodiments, for the source row the user may be able to select the desired row on the plate that contains the sample to use as the source in the well-to-well pipetting operation. In some embodiments, the user may be able to specify the source volume, or the volume of the sample to pipetted (e.g., in μL).

In some embodiments, the menu 1420 may include a well selector 1422, which may display a representation of all the wells in a plate. For example, FIG. 14B shows a 8×12 well plate having a total of 96 wells. The user may be able to highlight and select individual wells in the well selector 1422; selecting a well of the plate shown in the well selector 1422 may outline that well or change that well to a different color in order to indicate to the user that the well has been selected. The well-to-well pipetting operation of the protocol associated with the well-to-well pipetting block 1410 may be performed on the user-selected wells of the plate; selected wells of the plate may have samples from the source row pipetted into them.

In some embodiments, once the parameters associated with the well-to-well pipetting block 1410 are set by the user, the well-to-well pipetting block 1410 displayed in the user interface may update to show the state of the parameters set by the user. For instance, if the user selects specific wells within the well selector 1422 of the menu 1420, block 1410 may be visually updated in the user interface to block 1412 having a parameter state display 1414 and/or a parameter state display 1416. As seen in FIG. 14A, the parameter state display 1314 shows a representation of the user-selected wells in the plate. The user may be able to quickly glance at the block 1412 in the user interface in order to determine the selected wells without having to open the menu 1420 of FIG. 14B. The parameter state display 1416 shows the source row property; as seen in the figure, the parameter state display 1416 shows "F" which indicates the desired row on the plate that contains the sample to use as the source in the well-to-well pipetting operation.

Figure 15B:
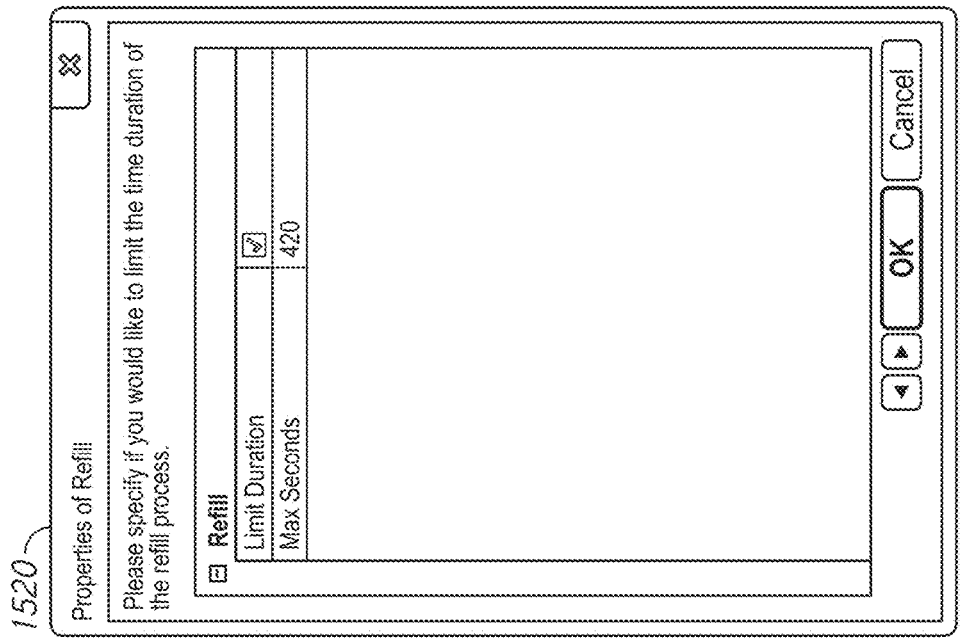
FIG. 15B illustrates an example embodiment of a user interface menu for setting parameters associated with a block.
Figure 15A:
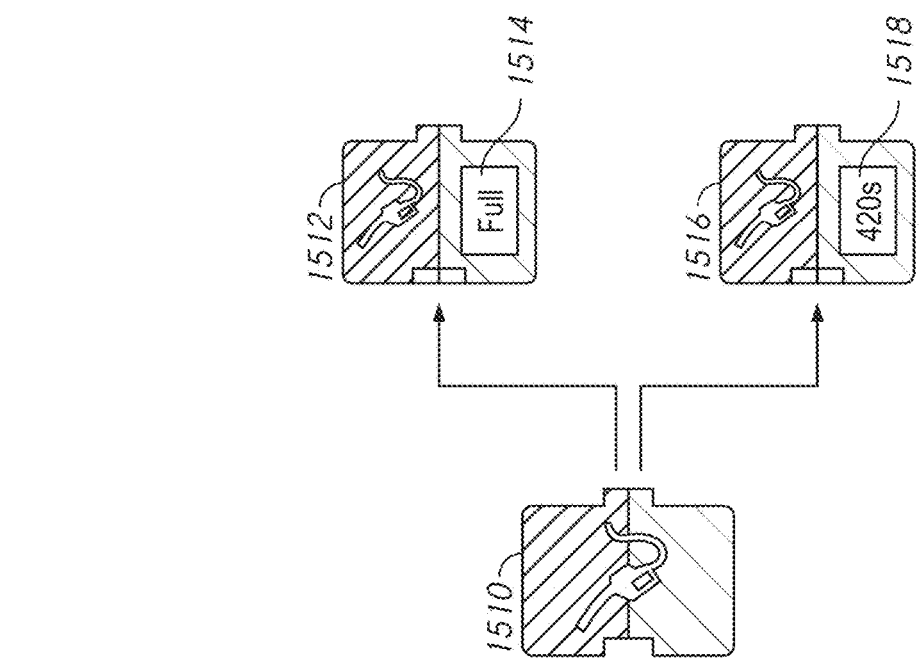
FIG. 15A illustrates an example embodiment of a block that a user may use in a graphical representation of a protocol.

FIG. 15A illustrates an example embodiment of a refill block that a user may use in a graphical representation of a protocol. FIG. 15B illustrates an example embodiment of a properties menu associated with the refill block.

More specifically, FIG. 15A illustrates an example embodiment of a refill block 1510. In some embodiments, block 1510 is a selectable graphical element within the visual protocol designer that corresponds to refilling one or more component of the flow cytometry machine, such as refilling the sheath tank of the instrument.

In some embodiments, the refill block 1510 displayed in the user interface of the visual protocol designer may change or update once the user sets the properties or parameters associated with block 1510, such as through menu 1520 shown in FIG. 15B. In some embodiments, the menu 1520 allows a user to set parameters such as a limit on the time duration of the refill process, and the max seconds for the time duration of the refill process. As seen in FIG. 15B, the menu 1520 includes a checkbox for limiting the duration. When the checkbox is unchecked, the sheath tank may be refilled until full. When the checkbox is checked, the time limit for refilling the sheath tank is enabled and the "Max Seconds" field is unlocked. In some embodiments, the "Max Seconds" field allows the user to set the desired time limit (in seconds) for refilling the sheath tank. In some of such embodiments, there may be a limited range for the time limit (e.g., the user may be limited to setting a time limit between 420-86400 seconds).

In some embodiments, once the parameters associated with the refill block 1510 are set by the user, the refill block 1510 displayed in the user interface may update to show the state of the parameters set by the user. For instance, if the user unchecks the checkbox for limiting the time duration within the menu 1520, block 1510 may be visually updated in the user interface to block 1512 having a parameter state display 1514. As seen in FIG. 15A, the parameter state display 1514 shows "Full" which may indicate to the user that the sheath tank will be refilled until it is full. Alternatively, if the user chooses to limit the time duration by checking the corresponding checkbox within the menu 1520 and sets the "Max Seconds" field, block 1510 may be visually updated to block 1516 having a parameter state display 1518. As seen in FIG. 15A, the parameter state display 1518 shows "420 s" which may indicate to the user that the limit duration property is activated and the time limit is set to 420 seconds.

Figure 16A:
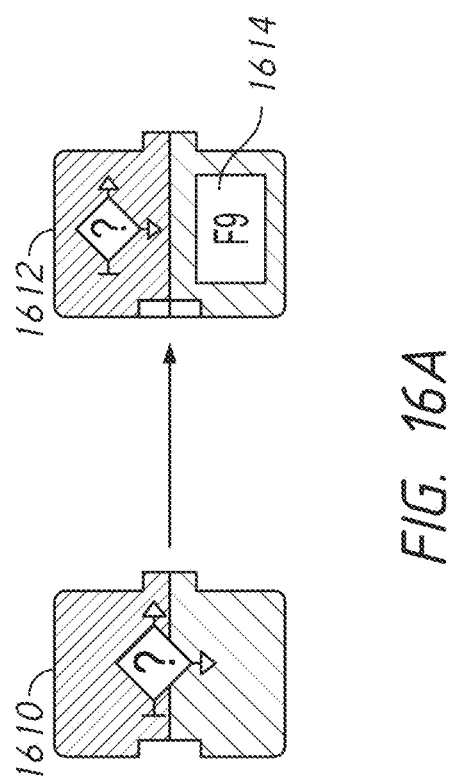
FIG. 16A illustrates an example embodiment of a block that a user may use in a graphical representation of a protocol.
Figure 16B:
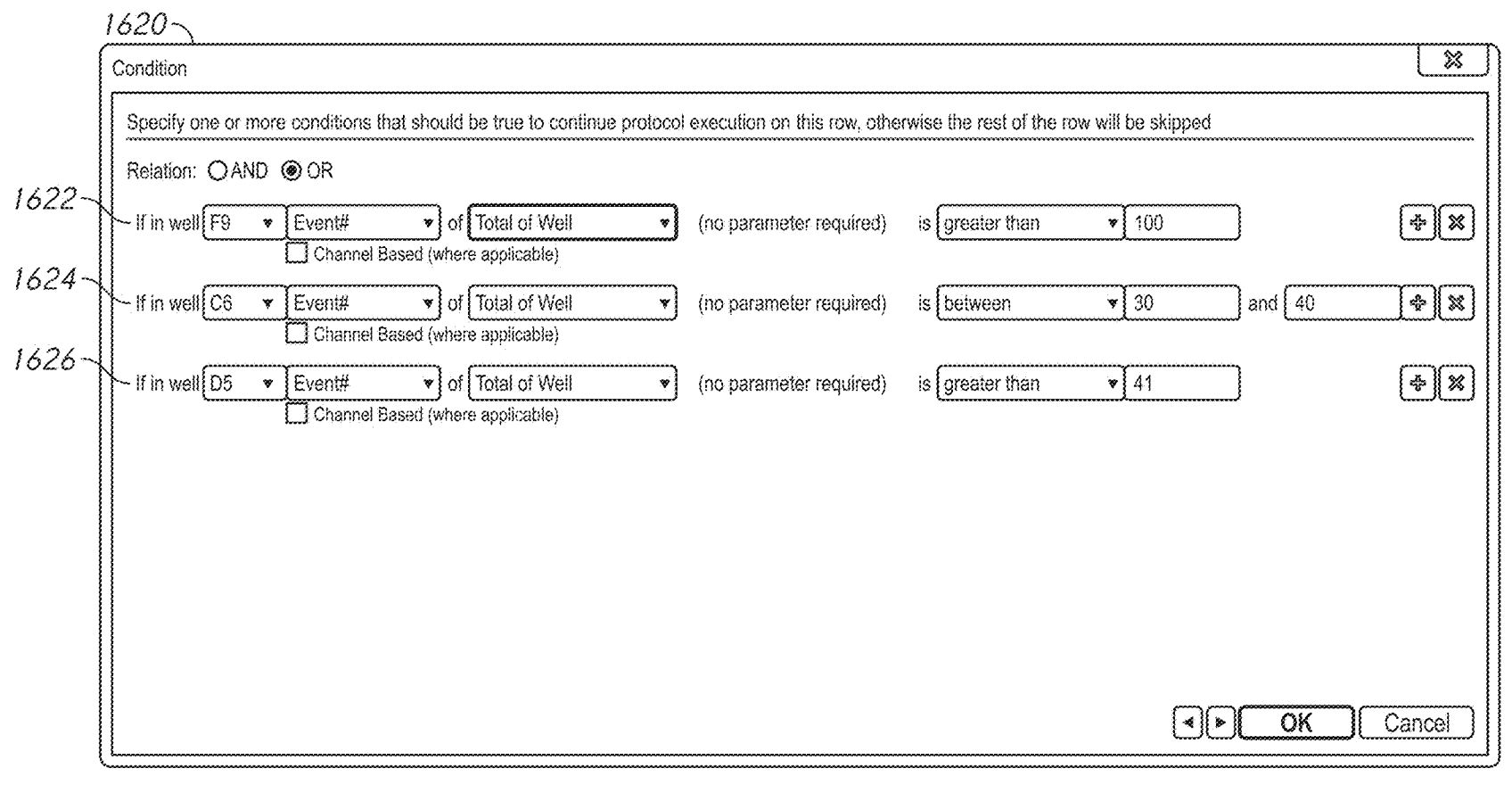

FIG. 16A illustrates an example embodiment of a conditional block that a user may use in a graphical representation of a protocol. FIG. 16B illustrates an example embodiment of a properties menu associated with the conditional block.

More specifically, FIG. 16A illustrates an example embodiment of a conditional block 1610. In some embodiments, block 1610 is a selectable graphical element within the visual protocol designer that a user may use to set a conditional statement that will execute all the subsequent blocks on the same row only if the condition is met (e.g., if conditions, while conditions, and so forth).

In some embodiments, the conditional block 1610 displayed in the user interface of the visual protocol designer may change or update once the user sets the properties or parameters associated with block 1610, such as through menu 1620 shown in FIG. 16B. In some embodiments, the menu 1620 allows a user to set various conditional statements for controlling the execution of instructions associated with other blocks in the graphical representation of the protocol. For example, the user may be able to add one or more conditional statements to be applied. In some embodiments, the user may be able to select the relation, or the desired Boolean relationship, between the statements (e.g., AND or OR). In some of such embodiments, this may only be applicable if there are two or more statements added by the user. For example, if the user selects the AND relation, all of the added conditional statements may need to be satisfied. Alternatively, if the user selects the OR relation, only one of the added conditional statements may need to be satisfied. For example, in FIG. 16B, the menu 1620 shows that the user added a total of three statements: statement 1622, statement 1624, and statement 1626. Since the user selected the OR relation, any of those statements can be satisfied before protocol execution is continued on the blocks in that row of the graphical representation of the protocol.

In some embodiments, the menu 1620 may have buttons to add conditional statements or delete each conditional statement. The user may be able to modify various aspects of each added conditional statement, such as target wells, population statistics, channel based, total of well, operator, and comparison number(s). For example, the target wells may include one or more user-selected wells to base the conditional statement on. The population statistics may include various desired statistics, including Event#, % of Parent, % of total, Absolute Count, Mode, Median, Mean, GMean, HMean, SD, CV, Robust SD, Robust CV, Skewness, and Kurtosis. The user may be able to select the checkbox for "Channel Based", where applicable. For an unchecked box, the conditional may be Value based (0-10000). For a checked box, the conditional may be Channel based (0-65535). For the conditional statement, the user may be able to select the desired operator for the statement, such as: less than, greater than, between, outside of, less or equal to, greater or equal to, and equal to. The user may also be able to select the comparison number(s) associated with the operator. For example, if the user selects the "less than" operator and sets the comparison number to 50, the conditional statement will be satisfied if some user-selected metric for the target well is less than 50.

In some embodiments, once the parameters associated with the conditional block 1610 are set by the user, the conditional block 1610 displayed in the user interface may update to show the state of the parameters set by the user. For instance, if the user selects a specific target well for a conditional statement within the menu 1620, block 1610 may be visually updated in the user interface to block 1612 having a parameter state display 1614. As seen in FIG. 16A, the parameter state 1614 shows "F9" which indicates the target well for at least one of the conditional statements associated with the block is the well in position F9.

Figures 17A, 17B:
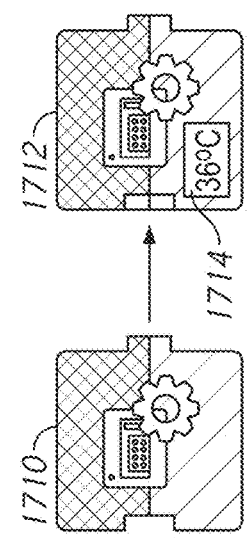
FIG. 17A illustrates an example embodiment of a block that a user may use in a graphical representation of a protocol.
FIG. 17B illustrates an example embodiment of a user interface menu for setting parameters associated with a block.

FIG. 17A illustrates an example embodiment of a cell incubator control block that a user may use in a graphical representation of a protocol. FIG. 17B illustrates an example embodiment of a properties menu associated with the cell incubator control block.

More specifically, FIG. 17A illustrates an example embodiment of a cell incubator control block 1710. In some embodiments, block 1710 is a selectable graphical element within the visual protocol designer that a user may use to control the climate parameters of an incubator component used with the flow cytometry machine.

In some embodiments, the cell incubator control block 1710 displayed in the user interface of the visual protocol designer may change or update once the user sets the properties or parameters associated with block 1710, such as through menu 1720 shown in FIG. 17B. In some embodiments, the menu 1720 allows a user to set climate parameters for the cell incubator, such as the temperature, humidity, carbon dioxide content, whether to shake plates, and the amount to shake the plates. For example, the user may be able to set a temperature (in Celsius), humidity (in % terms), carbon dioxide content (in % terms) to be maintained in the cell incubator. The user may be able to configure whether the cell incubator should shake the plates via the corresponding checkbox in menu 1720. If the checkbox is checked to enable shaking of the plates, the "Shake Amount (1/min)" field may be unlocked to allow the user to change the frequency at which to shake those plates (e.g., times per minute).

In some embodiments, once the parameters associated with the cell incubator control block 1710 are set by the user, the cell incubator control block 1710 displayed in the user interface may update to show the state of the parameters set by the user. For instance, if the user selects a specific temperature for the cell incubator within the menu 1720, block 1710 may be visually updated in the user interface to block 1712 having a parameter state display 1714. As seen in FIG. 17A, the parameter state 1714 shows "36° C." which indicates to the user that the temperature for the cell incubator is set to 36° C. without the user needing to check the menu 1720.

Figure 18B:
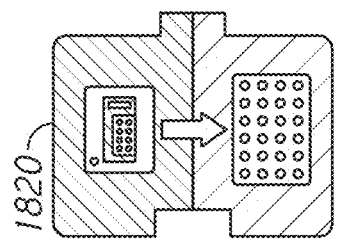
FIGS. 18A-B illustrate example embodiments of blocks that a user may use in a graphical representation of a protocol.
Figure 18A:
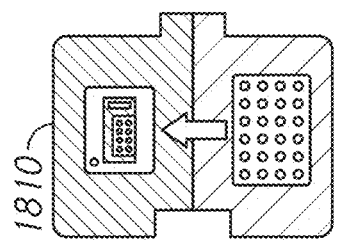

FIG. 18A illustrates an example embodiment of a put into cell incubator block that a user may use in a graphical representation of a protocol. More specifically, the figure shows a put into cell incubator block 1810. In some embodiments, block 1810 is a selectable graphical element within the visual protocol designer that a user may use to put a plate from the auto-sampler into the cell incubator. In some embodiments, there may be a menu associated with block 1810 that allows the user to set the properties or parameters associated with putting the plate into the cell incubator.

FIG. 18B illustrates an example embodiment of a get from cell incubator block that a user may use in a graphical representation of a protocol. More specifically, the figure shows a get from cell incubator block 1820. In some embodiments, block 1820 is a selectable graphical element within the visual protocol designer that a user may use to get a plate from the cell incubator (e.g., transfer a plate from the cell incubator to the auto-sampler). In some embodiments, there may be a menu associated with block 1820 that allows the user to set the properties or parameters associated with getting the plate into the cell incubator.

Figure 19:
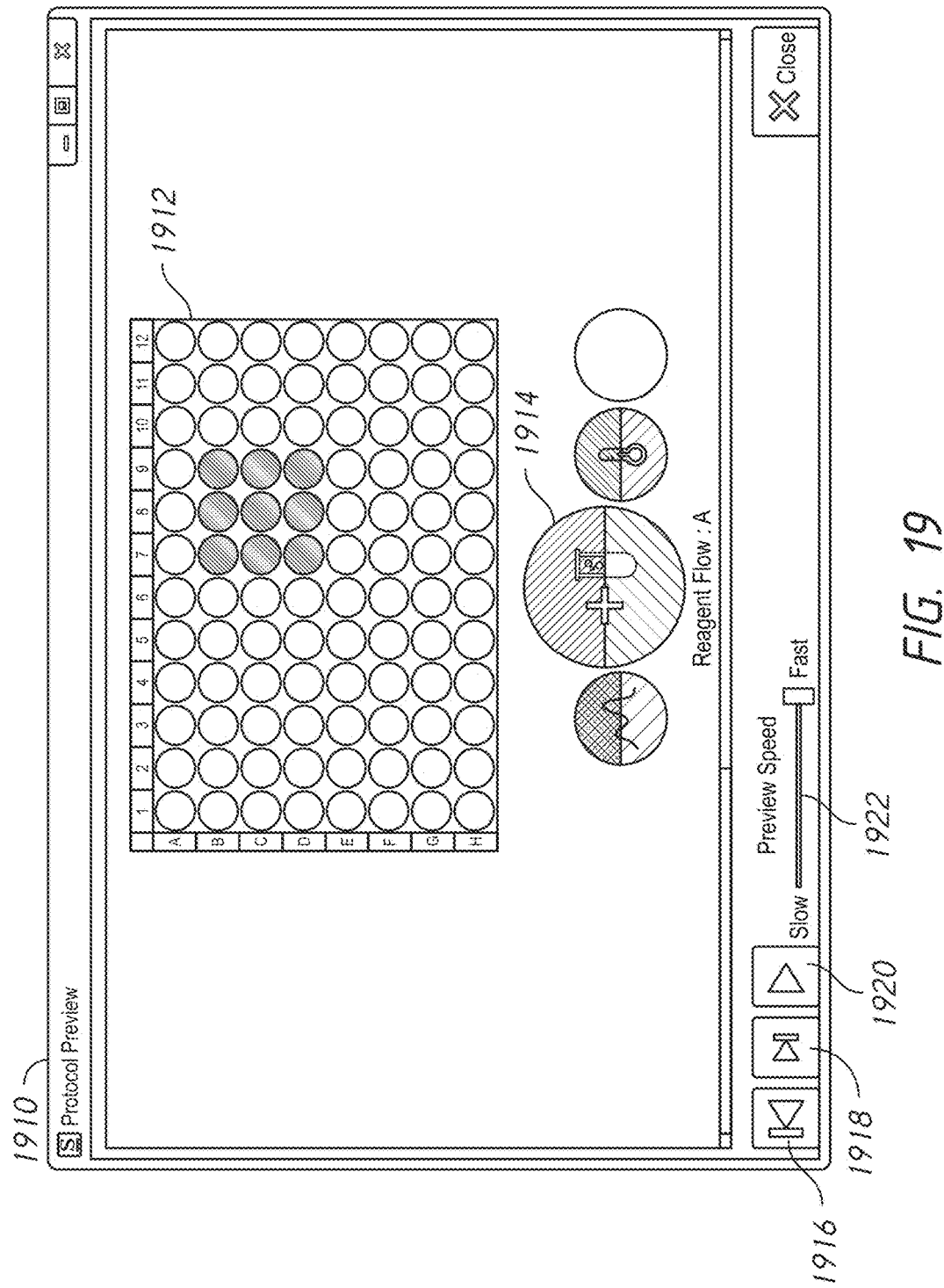
FIG. 19 illustrates an example embodiment of a protocol preview user interface.

FIG. 19 illustrates an example embodiment of a protocol preview user interface. More specifically, the figure shows a protocol preview window 1910, through which the user may preview or simulate how the protocol would be executed. In some embodiments, the protocol preview window 1910 may show the user how the corresponding instructions for each of the blocks in the graphical representation of the protocol are executed. In some embodiments, the protocol preview window 1910 may allow the user to step through each block and display the wells that are affected at each block.

In some embodiments, the protocol preview window 1910 may include a well preview 1912 which shows the wells affected in the operation corresponding to the currently selected block 1914 below the well preview 1912. The currently selected block 1914 may be one of the blocks in a row of the graphical representation of the protocol and may be displayed larger relative to the other blocks in the row. The well preview 1912 may highlight the wells associated with the current action in a certain color, and wells associated with other actions may be highlighted in a different color. For example, when a first block is the currently selected block 1914 the affected wells may be one color, and when the subsequent block is the currently selected block 1914 the affected wells may be a different color (and in some embodiments, the affected wells of the previous block may be concurrently highlighted).

In some embodiments, the well preview 1912 and currently selected block 1914 may playback and step through the blocks in the row sequentially, like a slideshow, at a rate associated with the slider 1922. The slider 1922 can be adjusted to change the preview speed and make it slower or faster. In some embodiments, there may be a previous button 1916 the user may select in order to make the previous block in the sequence the currently selected block 1914. In some embodiments, there may be a next button 1920 the user may select in order to make the next block in the sequence the currently selected block 1914. In some embodiments, there may be a play/pause button 1918 that the user may select to pause the playback of the preview of the blocks in the row, or to resume the playback from the paused state.

Terminology

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another, or may be combined in various ways. All possible combinations and sub-combinations are intended to fall within the scope of this disclosure. In addition, certain method or process blocks may be omitted in some implementations. And the inventions illustratively disclosed herein suitably may be practiced in the absence of any element which is not specifically disclosed herein. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method for programming protocols for a flow cytometry machine, the method comprising:
    generating a graphical user interface (GUI), the GUI comprising a workspace and a bank, wherein the bank includes a plurality of selectable graphical elements, wherein each selectable graphical element in the bank corresponds to program logic, and wherein each of the selectable graphical elements in the bank can be dragged over to the workspace;
    displaying the GUI to a user;
    receiving two or more first user inputs for dragging selectable graphical elements from the bank to the workspace of the GUI, wherein at least one of the selectable graphical elements is a conditional block;
    receiving a second user input selecting: one or more target wells, a metric for the one or more target wells, a comparison number, and a comparison operator describing a satisfactory relationship between the metric and the comparison number;
    updating the workspace of the GUI with a graphical representation for a protocol, wherein the graphical representation comprises an arrangement of the selectable graphical elements, and wherein the arrangement of the graphical representation conveys a sequence for performing the program logic corresponding to the selectable graphical elements;
    translating the graphical representation for the protocol into one or more executable instructions sent to a flow cytometry machine to perform the protocol, wherein the one or more executable instructions follows the sequence for performing the program logic corresponding to the selectable graphical elements conveyed by the graphical representation,
    wherein the program logic corresponding to the conditional block executes subsequent program logic in the sequence conveyed by the arrangement of the graphical representation only when the flow cytometry machine produces a metric by processing detected signals from a flow cytometer for the one or more target wells which satisfies the conditional relationship described by the second user input.

2. The method of claim 1, wherein the one or more executable instructions are configured to be translated back into the graphical representation for the protocol to be displayed in the GUI for additional editing of the graphical representation for the protocol.

3. The method of claim 1, wherein the program logic corresponding to at least one of the selectable graphical elements in the plurality of selectable graphical elements sets a reference point within the sequence conveyed by the arrangement of the graphical representation.

4. The method of claim 1, wherein the program logic corresponding to at least one of the selectable graphical elements in the plurality of selectable graphical elements controls a temperature associated with a component in the flow cytometry machine.

5. The method of claim 1, wherein the program logic corresponding to at least one of the selectable graphical elements in the plurality of selectable graphical elements controls an incubation period for a plate handled by the flow cytometry machine.

6. The method of claim 1, wherein the program logic corresponding to at least one of the selectable graphical elements in the plurality of selectable graphical elements controls recordation of contents of a plate handled by the flow cytometry machine.

7. The method of claim 1, wherein the program logic corresponding to at least one of the selectable graphical elements in the plurality of selectable graphical elements controls mixing of contents of a plate handled by the flow cytometry machine.

8. The method of claim 1, wherein the program logic corresponding to at least one of the selectable graphical elements in the plurality of selectable graphical elements controls the addition of a reagent to a plate handled by the flow cytometry machine.

9. The method of claim 1, wherein the GUI further comprises a preview window that displays to the user how the protocol would be executed based on the graphical representation for the protocol.

10. The method of claim 9, wherein the preview window is configured to separately display results from the program logic corresponding to a first selectable graphical element, of the selectable graphical elements, and the results from the program logic corresponding to a second selectable graphical element, of the selectable graphical elements.

11. The method of claim 1, wherein each selectable graphical element in the workspace is further configured to be selectable to modify a set of parameters associated with the program logic corresponding with that selectable graphical element.

12. The method of claim 1, wherein a first selectable graphical element, of the selectable graphical elements, is movable within the workspace to change the arrangement of the first and a second selectable graphical elements, of the selectable graphical elements.

13. The method of claim 1, wherein the method further comprises receiving a third user input for changing the arrangement of a first and a second selectable graphical elements, of the selectable graphical elements, in the workspace.

14. The method of claim 1, wherein the method further comprises receiving a third user input for modifying a set of parameters associated with the program logic corresponding with a first selectable graphical element, of the selectable graphical elements.

15. The method of claim 1, wherein the one or more executable instructions translated from the graphical representation is configured to be executed by a second flow cytometry machine different than the flow cytometry machine.

16. The method of claim 1, wherein the workspace of the GUI comprises an additional graphical representation for an additional protocol, and wherein translating the graphical representation for the protocol into one or more executable instructions includes translating the additional graphical representation for the additional protocol, and wherein the one or more executable instructions is further usable by the flow cytometry machine to perform the additional protocol sequentially with the first protocol.

17. The method of claim 1, wherein the GUI further comprises a well preview window that displays to the user a playback sequentially stepping through how the protocol is to be executed based on the graphical representation for the protocol.

18. A non-transitory computer readable media storing instructions that, when executed by one or more computing devices, cause the one or more computing devices to:
generate user interface data for displaying a user interface on a display screen, wherein the user interface is configured for managing a flow cytometry operation and comprises:
a block selection window for providing a plurality of selectable graphical elements, wherein each selectable graphical element corresponds to a set of program logic for performing a flow cytometry operation, wherein each selectable graphical element is configured to be dragged from the block selection window to the protocol visualization window, wherein at least one of the selectable graphical elements is a conditional block, wherein the conditional block is configured for user input to select: one or more target wells, a metric for the one or more target wells, a comparison number, and a comparison operator describing a satisfactory relationship between the metric and the comparison number; and
a protocol visualization window configured to receive one or more selectable graphical elements, including the conditional block, dragged over from the block selection window,
wherein any selectable graphical elements in the protocol visualization window may be independently movable within the protocol visualization window to create an arrangement of selectable graphical elements in the protocol visualization window,
wherein the arrangement of selectable graphical elements comprises a sequence of selectable graphical elements, including the conditional block,
wherein the conditional block executes subsequent program logic in the sequence conveyed by the arrangement of the graphical representation only when the flow cytometry machine produces a metric by processing detected signals from a flow cytometer for the one or more target wells which satisfies the conditional relationship described by the user input.

19. A computer system for implementing a flow cytometry environment, wherein the system comprises:
one or more components of a flow cytometry machine;
a computer system comprising:
one or more processors; and
a memory coupled with, and readable by, the processor and storing therein a set of instructions which, when executed by the processor, causes the one or more processors to:
generate graphical user interface (GUI) data for displaying a GUI on a display device, wherein the GUI comprises:
a block selection window for providing a plurality of selectable graphical elements, wherein each selectable graphical element corresponds to a set of program logic for performing a flow cytometry operation using one or more components of the flow cytometry machine, wherein each selectable graphical element is configured to be dragged from the block selection window to the protocol visualization window, wherein at least one of the selectable graphical elements is a conditional block, wherein the conditional block is configured for user input to select: one or more target wells, a metric for the one or more target wells, a comparison number, and a comparison operator describing a satisfactory relationship between the metric and the comparison number; and a protocol visualization window configured to receive one or more selectable graphical elements, including the conditional block, dragged over from the block selection window, wherein any selectable graphical elements in the protocol visualization window may be independently movable within the protocol visualization window to create an arrangement of selectable graphical elements in the protocol visualization window;

receive a graphical representation of a protocol, wherein the protocol is based on:

the arrangement of selectable graphical elements in the protocol visualization window, including the conditional block; and the corresponding set of program logic for each selectable graphical element in the arrangement; and translate the graphical representation of the protocol into one or more executable instructions for performing the protocol, wherein the one or more executable instructions are usable by the one or more components of a flow cytometry machine, wherein the conditional block executes subsequent program logic in the sequence conveyed by the arrangement of the graphical representation only when the flow cytometry machine produces a metric by processing detected signals from a flow cytometer for the one or more target wells which satisfies the conditional relationship described by the user input.

* * * * *